United States Patent [19]

Wolff et al.

[11] Patent Number: 4,933,367

[45] Date of Patent: Jun. 12, 1990

[54] CARBOXYLIC ACID DERIVATIVES, PROCESSES FOR THE PREPARATION THEREOF, THE USE THEREOF, AND PHARMACEUTICAL COMPOSITIONS WHICH CONTAIN THESE COMPOUNDS

[75] Inventors: Hans P. Wolff, Hirschberg-Grosssachsen; Ernst-Christian Witte, Mannheim; Hans-Frieder Kühnle, Weinheim, all of Fed. Rep. of Germany

[73] Assignee: Boehringer Mannheim GmbH, Mannheim, Fed. Rep. of Germany

[21] Appl. No.: 27,229

[22] PCT Filed: Jul. 10, 1986

[86] PCT No.: PCT/EP86/00406

§ 371 Date: Mar. 12, 1987

§ 102(e) Date: Mar. 12, 1987

[87] PCT Pub. No.: WO87/00521

PCT Pub. Date: Jan. 29, 1987

[30] Foreign Application Priority Data

Jul. 16, 1985 [DE] Fed. Rep. of Germany ....... 3525284

[51] Int. Cl.$^5$ .............. C07C 149/40; C07C 63/36; C07C 101/30; C07C 101/00; C07C 79/46; C07C 63/64; C07D 265/30; C07D 295/12; A61K 31/10; A61K 31/12; A61K 31/13; A61K 31/165; A61K 31/11

[52] U.S. Cl. .......................... 514/570; 514/231.2; 514/237.5; 514/238.2; 514/238.8; 514/239.2; 514/255; 514/317; 514/319; 514/330; 514/331; 514/510; 514/512; 514/517; 514/518; 514/519; 514/520; 514/522; 514/523; 514/524; 514/525; 514/530; 514/532; 514/533; 514/534; 514/535; 514/538; 514/539; 514/542; 514/543; 514/561; 514/562; 514/563; 514/564; 514/567; 514/568; 514/569; 260/404; 260/408; 260/410.5; 544/158; 544/159; 544/160; 544/161; 544/162; 544/163; 544/165; 544/167; 544/171; 544/383; 544/391; 546/230; 546/192; 546/205; 546/226; 546/232; 546/233; 546/235; 546/238; 546/239; 558/48; 558/52; 558/270; 558/271; 558/272; 558/389; 558/401; 558/403; 558/404; 558/406; 558/408; 558/409; 558/410; 558/412; 558/413; 558/414; 560/9; 560/11; 560/12; 560/13; 560/15; 560/16; 560/17; 560/20; 560/21; 560/22; 560/23; 560/37; 560/38; 560/39; 560/42; 560/43; 560/45; 562/426; 562/427; 562/429; 562/430; 562/433; 562/434; 562/435; 562/437; 562/438; 562/442; 562/452; 562/455; 562/456; 562/466; 562/471; 562/472; 562/478; 562/490; 562/493; 562/495; 562/496; 564/84; 564/86; 564/87; 564/88; 564/95; 564/97; 564/99; 564/152; 564/154; 564/155; 564/157; 564/158

[58] Field of Search .................. 558/48, 52, 412, 413, 558/414, 389, 401, 403, 404, 406, 408, 409, 410; 562/426, 427, 429, 430, 433, 434, 435, 437, 438, 442, 452, 455, 456, 457, 459, 466, 471, 472, 478, 490, 493, 495, 496; 260/404, 408, 410.5; 514/510, 512, 521, 522, 561, 562, 563, 564, 567, 568, 569, 570, 517, 518, 519, 520, 523, 524, 525, 530, 532, 533, 534, 535, 538, 539, 542, 543, 602, 603, 604, 616, 617, 618, 619, 620, 621; 564/84, 86, 87, 88, 95, 97, 99, 152, 154, 155, 157, 158; 560/9, 11, 12, 13, 15, 16, 17, 20, 21, 22, 23, 37, 38, 39, 42, 43, 45

[56] References Cited

FOREIGN PATENT DOCUMENTS 0025192 3/1981 European Pat. Off. ............ 514/518
2060443 6/1971 Fed. Rep. of Germany ...... 514/518
1382267 12/1971 United Kingdom ................ 562/429

OTHER PUBLICATIONS

Pallaud et al., C. R. Acad. Sci. Ser. C 273:711-713 (1971).
Chottard et al., C. R. Acad. Sci. 259:2653-2657 (1964).
Pattabiraman et al., Biochem. J. 126:645-657 (1972).
Mihara et al., Int. J. Peptide Protein Res. 23:447-453 (1984).
Kawai et al., Tetrahedron 34:3435-3444 (1978).
Vieweg et al., Pharmazie 38:22-24, 818-820 (1983).
Ansell et al., J. Chem. Soc. Perkins Trans. 1:2789-2795 (1973).
Atkinson et al., J. Chem. Soc., Perkins Trans. 1:394-401 (1974).
Chottard et al., Tetrahedron 25:4967-4983 (1969).
Gardner et al., J. Org. Chem. 22:1704-1705 (1957).
Trost et al., J. Am. Chem. Soc. 1983, 105, 7757-7759.
Trost et al., J. Org. Chem., Vol. 43, No. 23, 1978, pp. 4549-4551.

Primary Examiner—Mary C. Lee
Assistant Examiner—Johann Richter
Attorney, Agent, or Firm—Felfe & Lynch

[57] ABSTRACT

This invention relates to carboxylic acid derivatives and their use thereof. The compounds are useful in treatment of various diseases such as diabetes, prediabetic conditions, adipositas ailments or atherosclerosis.

22 Claims, No Drawings

CARBOXYLIC ACID DERIVATIVES, PROCESSES FOR THE PREPARATION THEREOF, THE USE THEREOF, AND PHARMACEUTICAL COMPOSITIONS WHICH CONTAIN THESE COMPOUNDS

The subject of the present invention is new carboxylic acid derivatives of the general formula I

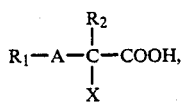

wherein
$R_1$ is a substituted or unsubstituted aryl or aryloxy moiety,
$R_2$ is a hydrogen atom, a low alkyl moiety, or the group $R_1$-A-, and, in the case where X represents the cyano group, an acylamino group or amino group,
A is a straight-chain or branched, saturated or unsaturated alkylene group with 3–8 carbon atoms which has a chain length of at least 3 carbon atoms,
X is the cyano group or a group of the formula -B-$R_3$, or -D-$NR_4R_5$, in which
B is O, S, SO, $SO_2$, O(CO), $OSO_2$, NHCO, $NHSO_2$ or CO,
D is a valency bond, $SO_2$ or CO,
$R_3$ is an alkyl, trifluoromethyl, cycloalkyl, aralkyl, aralkenyl or aryl group, the aryl moiety can be substituted,
$R_4$ is hydrogen, a low alkyl moiety, a substituted or unsubstituted aryl or aralkyl moiety,
$R_5$ is hydrogen, a low alkyl moiety, or
$R_4$ and $R_5$ are an alkylene chain with 4–6 carbon atoms which can be interrupted by O, S or $NR_6$, and
$R_6$ is hydrogen, a low alkyl moiety or a substituted or unsubstituted phenyl or benzyl moiety,
as well as their physiologically acceptable salts, esters, amides and nitriles, provided that, in the case
(a) in which A is an alkylene group with 3 carbon atoms,
   (a1) in no case can the aryl moiety of group $R_1$ be the unsubstituted phenyl moiety and
   (a2) X must not be the groups —CN, —$NHCOR_3$ and $NR_4R_5$;
(b) in which X is a moiety of the formula —$SCH_3$, $R_2$ must not be methyl,
(c) in which X is the group —$NH_2$ or =$NHCOCH_3$, $R_1$A- must not be 4-phenylbutyl or 4-(4-methoxyphenyl)butyl,
(d) in which X is the group 2,4-dinitrophenyl, $R_1$A- must not be 4-phenylbutyl or 5-phenylpentyl,
(e) in which X is the group —$COCH_3$, $R_1$A- must not be 3-(2-chlorophenyl)propyl or 5-(4-methoxyphenyl)pentyl.

Of the compounds of the general formula I only a few examples have been known heretofore, with the exception of the norvaline analogues (A=—$(CH_2)_3$— and X=$NR_4R_5$ and $NHCOR_3$). The pharmacological action according to the invention has not yet been described in these cases:
2-cyano-5-phenylpentanoic acid and derivatives with substituents on the aromatic ring are described as reaction products (Pallaud et al., C.R. Acad. Sci., Ser. C 1971, 273, 711)
2-cyano-7-phenylheptanoic acid is also described as a reaction product (Julia et al., Bull. Soc. Chim. Fr. 1968, 3691; Chottard et al., Compt. Rend. 1964, 259, 2653)
2-phenoxy-5-phenylpentanoic acid is described by Nordin in U.S. Pat. No. 3,562,330, as a precursor of antiarrhythmically active amines.
5-phenyl-2-phenylsulfonyl-4-pentanoic acid methyl ester is described by Trost and Hung, J. Am. Chem. Soc. 1983, 105, 7757, as an intermediate.
2-methyl-2-methylthio-5-phenylpentanoic acid and phenyl-substituted analogues, as well as 2-methyl-2-methylthio-6-(3-methoxyphenyl)hexanoic acid and 2-methyl-2-methylthio-7-(3,4-methylenedioxyphenyl)heptanoic acid are described by Trost et al., J. Org. Chem. 1978, 43, 4549, as intermediates for the production of enol thioethers.

Besides the already-mentioned norvaline analogues (A=—$(CH_2)_3$—), the following have also already been described as derivatives with an amino function:
(a) 2-amino-6-phenylhexanoic acid and its N-acetyl derivative, by Pattabiraman et al., Biochem. J. 1972, 126, 645, by Kosui et al., Mem. Fac. Sci., Kyushu Univ., Ser. C 1981, 13, 89, and by Hashimoto et. al., Int. J. Pept. Protein Res. 1983, 21, 11.
(b) 2-amino-6-(4-methoxyphenyl)hexanoic acid and the N-acetyl derivative, by Kosui et al., Bull. Chem. Soc. Jpn. 1982, 55, 918 and by Mihara et al., Int. J. Pept. Protein Res. 1984, 23, 447.
(c) 2-[(2,4-dinitrophenyl)amino]-6-phenylhexanoic acid, and 2-[(2,4-dinitrophenyl)amino]-7-phenylheptanoic acid by Kawai et al., Tetrahedron Lett. 1975, 2845 and Tetrahedron 1978, 34, 3435.
(d) 2-arylsulfonylamino-5-phenylpentanoic acids: by Vieweg and Wagner in Pharmazie 1983, 38, 22, with 4-cyanophenyl as aryl moiety, and by Vieweg and Wagner in Pharmazie 1983, 38, 818, with 4-methylphenyl and 1-naphthyl as aryl moieties. The two last-named substances are intermediates for the preparation of potential serine proteinase inhibitors.
(e) 2-acetyl-5-phenylpentanoic acid is described by Answell et al., J. Chem. Soc. Perkin Trans. 1, 1973, 2789, and Kaye et al., DOS 2,060,443, and 2-acetyl-5-(2-chlorophenyl)pentanoic acid, by Amschler et al., Eur. Pat. Appl. 25,192. The latter serves for the preparation of antidiabetically active substances. However, no pharmacological action is attributed to the intermediate.
(f) 2-acetyl-7-(4-methoxyphenyl)heptanoic acid is described by Atkinson and Green, J. Chem. Soc., Perkin Trans. 1, 1974, 394, as a reaction product.
(g) 2-acetoxy-5-phenylpentanoic acid methyl ester is described by Chottard et al., Tetrahedron 1969, 25, 4967, and 2-aminocarbonyl-5-phenylpentanoic acid by Gardner and Brandon, J. Org. Chem. 1957, 22, 1704, as reaction products.

The compounds of general formula I possess valuable pharmacological properties. They can be used for the treatment of diabetes, prediabetes, and especially for the treatment of diabetes of the aging.

The compounds of general formula I have no relationship to known antidiabetic compounds either structurally or in the nature of their action. They lower the blood sugar level by an increase of the peripheral glucose oxidation, their action depending upon an increase of the sensitivity of peripheral tissues towards insulin. In contradistinction to the biguanides, no increase of the blood lactate levels is observed. Therefore, the compounds of general formula I are also valuable for the treatment of nondiabetic illnesses in which insulin resistance is present, as for example adipositas and atherosclerosis.

It has furthermore been found that the antidiabetic effectiveness is not limited to the new compounds of the general formula I with the meanings given above for $R_1$, $R_2$, A and X, but also that already-known derivatives which are included by the general formula I', with the following, expanded meaning of $R_1'$, $R_2'$, A' and X', possess this new-found effectiveness:

Subject matter of the application therefore are also pharmaceuticals for the treatment of diabetes, prediabetes, adipositas and atherosclerosis, which contain carboxylic acid derivatives of the general formula I',

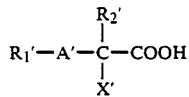

wherein
$R_1'$ represents hydrogen or a substituted or unsubstituted aryl or aryloxy moiety,
$R_2'$ represents hydrogen, a low alkyl moiety, or the group $R_1$-A'-, and, in the case in which X represents the cyano group, an acylamino or amino group,
A' represents a straight-chain or branched, saturated or unsaturated alkylene group having 1-18 carbon atoms,
X' represents the cyano or carbethoxy group or a group of the formula -B-$R_3$ or -D-$NR_4R_5$,
wherein
B represents O, S, SO, $SO_2$, O(CO), $OSO_2$, NHCO, $NHSO_2$ or CO, and
D represents a valency bond, $SO_2$ or CO,
$R_3$ represents an alkyl, trifluoromethyl, cycloalkyl, aralkyl, aralkenyl or aryl group, whose aryl moiety can be substituted in each case,
$R_4$ hydrogen, a low alkyl moiety, a substituted or unsubstituted aryl or aralkyl moiety,
$R_5$ hydrogen, a low alkyl moiety, or
$R_4$ and $R_5$ together, an alkylene chain having 4-6 carbon atoms, which can be interrupted by O, S or $NR_6$, and
$R_6$ hydrogen, a low alkyl moiety, or a substituted or unsubstituted phenyl or benzyl moiety,
as well as their physiologically acceptable salts, esters, amides and nitriles.

Aryl moieties are to be understood to be aromatic hydrocarbons with 6 to 14 carbon atoms, preferably the phenyl and naphthyl group.

Substituted aryl moieties are to be understood in all definitions to be all those aromatic hydrocarbons of 6 to 14 carbon atoms which have in one or more positions the hydroxyl group, halogen, a low alkyl, low alkoxy, trifluoromethyl, cyano, or nitro group, or an amino group which can be substituted in one or two positions by low alkyl. In particular, phenyl or naphthyl moieties, substituted in some cases by the above-named groups, can serve as such. Especially preferred is the phenyl and the 4-chlorophenyl moiety. Halogen is here to be understood to be fluorine, chlorine, bromine and iodine, preferably fluorine, chlorine and bromine.

The aryloxy moiety contains an aromatic hydrocarbon moiety with 6 to 14 carbon atoms and preferably a phenyl moiety. Substituted aryloxy moieties are to be understood as those which are substituted in the same manner as the above-named aryl moieties, the 4-chlorophenoxy moiety being preferred.

Unbranched alkylene chains A are to be understood to be preferably the following:

n in formula I = 3-8, —CH=CHCH_2—,
n in formula I' = 1-18, —C≡CCH_2.
the groups:

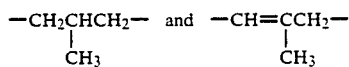

are to be understood to be preferred as branched groups A.

The alkyl groups of the moieties $R_3$ are to be understood to be straight-chain or branched hydrocarbons with 1 to 8 carbon atoms, especially the methyl and the octyl group.

The cycloalkyl moieties of group $R_3$ can contain 5 to 7 carbon atoms in the ring system. The cyclohexyl moiety is preferred.

The aralkyl and aralkenyl moieties of group $R_3$ are to be understood as being saturated or unsaturated alkyl moieties having 1-4 carbon atoms, which are substituted by an aryl group, substituted if desired, as defined above. Of these the 2-phenylethyl moiety and the 2-phenylethyl moiety are to be understood as preferred.

The low alkyl moieties of groups $R_4$, $R_5$ and $R_6$ are to be understood to be hydrocarbon moieties with 1 to 4 carbon atoms, especially the methyl and ethyl moiety.

Aralkyl moieties of groups $R_4$ and $R_6$ are to be understood to be alkyl moieties with 1-3 carbon atoms, which are substituted by an aryl group according to the definition given above, which is substituted if desired. Preferred among these is the benzyl moiety.

A group $NR_4R_5$, in which the moieties $R_4$ and $R_5$ together form an alkylene chain which can be interrupted by O, S or $NR_6$, is to be understood to mean saturated nitrogen heterocyclics with 5–6 ring atoms, which can additionally contain in any position an oxygen, sulfur or nitrogen atom. Of these, the piperidino, morpholino, 5-methylpiperazino, 5-phenylpiperazino and 5-benzylpiperazino groups are to be understood to be preferred.

A group of the formula —B—$R_3$ or —D—$NR_4R_5$ is to be understood to mean preferably the following:
—CN, —COOC_2H_5, —OCH_3, —S—CH_3, —SOCH_3, —SO_2CH_3, —SO_2CF_3, —O—phenyl, —S—phenyl, —SO—phenyl, —SO_2—phenyl,
—SO_2-naphthyl, —SO_2CH_2CH_2-phenyl, —SO_2—CH=CH-phenyl, —OCOCH_3, —OSO_2CH_3, —NHCOCH_3, —NHSO_2CH_3, —COCH_3, —OCO-phenyl, —OSO_2-phenyl, —NHCO-phenyl, —NH-SO_2-phenyl, —CO-phenyl,
—NH_2, —N(C_2H_5)_2, —NH-phenyl, —NH-benzyl, -morpholino, -piperidino, -4-benzylpiperazino, —SO_2NH_2, —SO_2N(C_2H_5)_2, —SO_2-piperidino, —CONH_2, —CON(CH_3)_2, —CO—N(C_2H_5)_2, —CO—NH-phenyl, —CO—NH-benzyl, —CO-piperidino, —CO-morpholino, —CO—(4-phenylpiperazino), —CO—(4-benzylpiperazino),
the phenyl ring in all cases being able to be substituted by the substituents listed above.

For the person skilled in the art it is obvious that, in the case of an unsaturated alkylene chain A, any aryloxy substituent $R_1$ that might be present must be separated from the double bond by at least one saturated carbon atom, since otherwise the group $R_1$—A— would have to be understood to cover reactive enol ethers.

The physiologically acceptable salts are especially alkali, alkaline-earth or ammonium salts (plus salts with blood sugar-lowering biguanides if desired).

The esters derived from the carboxylic acids of general formula I contain as alcohol components low univalent alcohols, of which methanol, ethanol and n-butanol are preferred, as well as polyvalent alcohols such as glycerine, or alcohols with other functional groups, such as ethanolamine for example.

The amides according to the invention, derived from the carboxylic acids of general formula I, contain as amine component preferably ammonia, p-aminobenzoic acid, β-alanine, ethanolamine or 2-aminopropanol. However, alkylamines, such as isopropylamine or tert.-butylamine, dialkylamines such as diethylamine, and cyclic amines such as morpholine or 4-substituted piperazines, for example, are also included.

The substituted carboxylic acids of general formula I have a center of chirality. The above definition of the compounds according to the invention therefore also include all possible enantiomers, their mixtures, and the racemates.

Also subject matter of the invention are processes for the preparation of the compounds of general formula I, in which (A) in a known manner, a compound of general formula II,

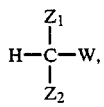
(II)

in which
$Z_1$=—COOR$_7$, —CN, —CO—R$_3$, —SO—R$_3$, —SO$_2$—R$_3$, —CONH$_2$ or —SO$_2$NH$_2$,
$Z_2$=hydrogen, low alkyl or —NH—R$_8$
W=—COOR$_7$ or another group that can be converted to the carboxyl function,
$R_7$=low alkyl, and
$R_8$=an amino protective group,
and $R_2$ has the same meaning given above, is alkylated with (a1) a compound of the general formula III, $R_1$—A—Y  (III)

in which $R_1$ and A have the meaning given above and Y is a reactive moiety, or (a2) in the case in which $Z_2$ represents hydrogen, is condensed with a compound of the general formula III'

$R_1$—A'—CHO  (III')

in which A' represents an alkylene moiety with the CH$_2$ group removed and $R_1$ has the meaning given above, and after the condensation the double bond that has developed is hydrogenated, and (b) the compounds of the general formula IV

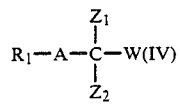

are converted if desired, e.g.:

(b1) in the case where $Z_2$ represents hydrogen, by alkylating again with a compound of the general formula V, $R_2$—Y  (V)

in which $R_2$ has the meaning given above and Y represents a reactive group, or, (b2) in the case where $Z_1$, COOR$_7$ and $Z_2$ represent the group —NH—R$_8$, the moiety $R_8$ is transformed by methods known in themselves to the moieties —CO—R$_3$ or —SO$_2$—R$_3$ or, (b3) in the case where $Z_1$, COOR$_7$ and $Z_2$ represent hydrogen, the hydrogen atom is replaced with a halogen atom in a manner known in itself with a halogenating agent, and then the moiety $Z_1$ is transformed to a hydrogen atom by decarboxylation, and the reactive derivative IV, in which $Z_2$ is now halogen and $Z_1$ is now hydrogen, is reacted either with a compound of the formula VI,

H—B—R$_3$  (VI)

in which B represents O, S or NHSO$_2$ and R$_3$ has the meaning given above,
to form the compound

or with a compound of formula VI',

NHR$_4$R$_5$  (VI')

in which R$_4$ and R$_5$ have the meaning given above, to form the compound

and
(c) after the condensation, in the case where
(c1) B represents a sulfur atom, it is oxidized by methods known in themselves, if desired, to form the sulfoxides and sulfones, or (c2) by transposing the reactive derivative IV, wherein $Z_1$ represents hydrogen and $Z_2$ halogen, with sodium sulfite, and converting the compound IV thus obtained, in which $Z_2$ now represents —SO$_3$H, to the group —SO$_2$NR$_4$R$_5$, and, after these conversions of compounds IV, if performed, the groups W and, if desired, $Z_1$ are transformed to the free carboxylic acids, or their salts, esters or amides.

(B) Another method of preparing the compounds of general formula I is to react a compound of the general formula IV, wherein $Z_1$ and $Z_2$ together represent an oxo function, first with a reducing agent or an organometallic compound of the general formula VII $$R_2-M \qquad (VII)$$

in which $R_2$ has the meaning given above and M represents an alkali metal or alkaline earth metal, and the compound IV obtained, in which $Z_1$ now represents a moiety of the formula $R_2$ and $Z_2$ a hydroxyl group, is acylated in a known manner with a sulfonyl chloride of the general formula VIII, $$R_3-SO_2Cl \qquad (VIII)$$

or with a carboxylic acid chloride of the general formula IX $$R_3-COCl \qquad (IX)$$

in which $R_3$ has the meaning given above, and then, if desired, the group W is converted to the free carboxylic acid, or its salts, esters or amides.

In alkylations according to method (a1) either the halides, especially the chlorides and bromides, or else appropriate sulfonic acid esters, such as mesylates or tosylates, are used.

The reaction of the halides or sulfonic acid esters with the compounds of general formula II is best performed with the addition of a strong base, such as sodium methylate, sodium hydride or 1,8-diazabicyclo(5,4,0)undec-7-ene. Ethanol, dimethylsulfoxide or benzene, for example, serve as inert solvents. Also to be considered as solvents are, for example, dimethyl formamide or hexamethylphosphoric acid triamide. The reaction is performed preferably at room temperature or moderately elevated temperature, or at the boiling temperature of the solvent.

The reaction of compounds II with aldehydes or formula III' by method (a2) is performed under conditions such as those commonly used for a condensation of activated methylene groups with keto compounds. Preferably the condensation is performed in pyridine or dimethyl formamide with the addition of catalytic amounts of a strong base such as piperidine, for example.

It is advantageous to add a suitable solvent, such as benzene, to the reaction mixture, in order to distill the reaction water azeotropically.

The subsequent hydrogenation of the double bond is performed in a conventional manner with catalytically activated hydrogen, at standard pressure or at elevated pressure. The catalysts can be metal catalysts, such as Raney nickel or palladium charcoal, for example. Acetic acid or low alcohols are suitable solvents, and also aqueous alkali in the case of carboxylic acids IV.

An amino protective group $R_3$ is to be understood to be, for example, acyl groups, such as the formyl or acetyl group. However, other protective groups can be used, such as those used in peptide syntheses. For the conversion of a compound of the general formula IV with a protective amino group ($Z_1 = -NH-R_5$) to a drivative IV, $Z_1 = -NH-SO_2-R_3$, first the group $R_5$ is split off in the usual manner, e.g., in the case of acyl groups by saponification with dilute alkali lye or dilute mineral acid. Then the free amino acid obtained is acylated in a conventional manner with a sulfonyl chloride of the general formula VIII, preferably after protecting the carboxyl function, e.g., by esterification. In the case of aromatic sulfonyl chlorides, the reaction can also be performed by the "Schotten-Baumann" method. If it is desired to operate under anhydrous conditions, absolute pyridine is preferably used. However, other tertiary bases can be used, such as dimethylaniline or triethylamine, in an inert solvent such as methylene chloride, for example. Instead of the free amino acids, their salts can also be used.

For the halogenation of compounds of the general formula IV with $Z_2=H$, sulfuryl chloride, N-chlorosuccinimide and N-bromosuccinimide are used chiefly. Reactions with N-chloro- and N-bromosuccinimide are preferably performed in an inert solvent such as tetrahydrofuran, at room temperature or moderately elevated temperature. The reaction is best performed without solvents, with heating, preferably at 50°-80° C.

The decarboxylation of compounds of the general formula IV, in which W and $Z_1$ represent the group $-COOR_4$, is best performed simultaneously with the saponification of the corresponding esters, by methods known in themselves. Preferably the decarboxylation is performed in a mixture of 6N hydrochloric acid and glacial acetic acid, or in caustic soda solution, at ebullition.

The reaction of the α-halogenocarboxylic acids of the general formula IV, wherein $Z_1$ represents hydrogen and $Z_2$ halogen, with the compounds of general formula VI, is best performed with the addition of an acid-binding agent such as sodium hydrogen carbonate, sodium carbonate, potassium carbonate, sodium methylate or sodium hydride. Esters of the α-halo acids are preferably used for the reaction. Ether, benzene, tetrahydrofuran, dioxane or methylene chloride are used, for example, as inert solvents. When inorganic bases are used, ethanol, butan-2-one, dimethylformamide, hexamethylphosphoric acid triamide, or acetonitrile are also used, for example, as the reaction medium.

The reactions are performed at room temperature or at elevated temperature, preferably at the boiling temperature.

The oxidation of compounds of general formula IV', in which B represents a sulfur atom, to sulfoxides or sulfones is preferably performed with hydrogen peroxide in polar solvents such as glacial acetic acid, a mixture of glacial acetic acid and acetic anhydride, or acetone. Oxidation with trifluoroperacetic acid has proven especially advantageous. Trifluoroacetic acid is used preferentially in this case as solvent.

The reaction of compounds of general formula IV in which $Z_1$ represents hydrogen and $Z_2$ halogen, with sodium sulfite, is performed in a manner known in itself by heating the components in aqueous solution. The sulfocarboxylic acids thus obtained are converted in a conventional manner, e.g., by thionyl chloride, to the reactive sulfochlorides, and these are then reacted with ammonia to produce the desired amidosul-fonyl derivatives.

The reduction of compounds of the general formula IV, wherein $Z_1$ and $Z_2$ together represent an oxo group, by method B can be performed conventionally with catalytically activated hydrogen. Preferred in this case is hydrogenation at standard pressure or at elevated pressure in the presence of metal catalysts such as palladium or Raney nickel in solvents such as, for example, acetic acid or low alcohols.

The reduction can also be performed, if desired, with complex metal hydrides. Sodium hydroboride is used preferentially. In this case the reaction can be performed in an alcohol, especially in methanol, or in dioxane or in an aqueous-alkaline milieu.

The reaction of compounds of general formula IV, in which $Z_1$ and $Z_2$ together represent an oxo function, with organometallic compounds of formula VII by method b takes place in inert solvents such as diethyl ether or tetrahydrofuran. The subsequent acylation of the compounds IV thus formed, in which $Z_1$ now represents $R_2$ and $Z_2$ the hydroxyl group, with a compound of the general formula VIII is performed by methods such as those described above for the acylation of the amino acids. The reaction is performed preferably in pyridine as solvent.

The group W, which can be converted to a carboxyl function, is to be understood especially as the nitrile group or a moiety which can be converted by oxidation to the carboxyl function. The preferred oxidizable groups are the hydroxymethyl group, the aminomethyl group and the formyl group, or functional derivatives of these groups. The oxidation can be performed with the conventional oxidants, such as manganese IV compounds, permanganates, dichromates and, in the case of the formyl group, also with atmospheric oxygen and silver oxide.

The conversion of the substituents W and $Z_1$ which is to be performed directly after the condensation to compounds of general formula IV is performed, for example, by saponifying the carboxylic acid esters to the corresponding carboxylic acids with mineral acids or alkali hydroxides in a polar solvent (such as water, methanol, ethanol, dioxane or acetone). The saponification is advantageously performed with a strong base (such as sodium hydroxide or potassium hydroxide) in a mixture of methanol and water at room temperature or at moderately elevated temperatures. Vice-versa, however, the carboxylic acids can be esterified in a conventional manner, or esters with another moiety $R_4$ can be converted by esterification to an ester with a different moiety $R_4$. The esterification of the carboxylic acids is preferably performed in the presence of an acid catalyst, such as, for example, hydrogen chloride, sulfuric acid, p-toluenesulfonic acid, or a strongly acid ion exchange resin.

Transesterifications, however, require the addition of a small amount of a basic substance, e.g., of an alkali or alkaline earth hydroxide or of an alkali alcoholate. For the esterification of the carboxyl group or for a transesterification, basically any alcohols are suitable. Preferred are the low univalent alcohols, such as methanol, ethanol or propanol, as well as polyvalent alcohols, e.g., glycerol, or alcohols with other functional groups, such as ethanolamine, for example.

The amides according to the invention, derived from the carboxylic acids of general formula I, are preferably prepared by methods known in themselves from the carboxylic acids or their reactive derivatives (such as, for example, carboxylic acid halides, esters, azides, anhydrides or mixed anhydrides) by transposition with amines. The amine components are, for example, ammonia, alkylamines and dialkylamines, but also amino alcohols, such as ethanolamine and 2-aminopropanol, as well as amino acids such as p-aminobenzoic acid, β-alanine and others. Other valuable amine components are alkyl-, aralkyl- and arylpiperazines.

The preparation of the above amides, however, can also be performed by partial saponification of the nitriles derived from the carboxylic acids according to the invention. The saponification is performed in dilute mineral acids at moderately elevated temperatures, in alkaline hydroperoxide solution, or, advantageously, in 98% sulfuric acid or polyphosphoric acid.

For the preparation of salts with pharmacologically compatible organic or inorganic bases, such as, for example, sodium hydroxide, potassium hydroxide, calcium hydroxide, ammonium hydroxide, methylglucamine, morpholine or ethanolamine, the carboxylic acids can be reacted with the corresponding bases. Mixtures of the carboxylic acids with a suitable alkali carbonate or alkali hydrogen carbonate, can also be used.

For the preparation of pharmaceutical products, the compounds of the general formula I are mixed in a known manner with suitable pharmaceutical excipients, flavorings, scents and dyes, and put into the form of tablets or dragees, or suspended or dissolved in water or oil, such as olive oil for example.

The substances of general formula I can be administered orally and parenterally in liquid or solid form. The preferred injection medium is water containing the stabilizers, solubilizers and/or buffers commonly used in injection solutions. Such additives are, for example, tartrate or borate buffers, ethanol, dimethylsulfoxide, complexing agents (such as ethylenediaminetetraacetic acid), polymers of high molecular weight (such as liquid polyethylene oxide) to control viscosity, or polyethylene derivatives or sorbitol anhydrides.

Solid excipients include, for example, starch, lactose, methyl cellulose, talc, highly dispersed silica, high-molecular-weight fatty acids (such as stearic acid), gelatine, agar-agar, calcium phosphate, magnesium stearate, animal and vegetable fats and high-molecular-weight polymers (such as polyethylene glycols). Compositions suitable for oral administration can, if desired, contain flavoring and sweetening agents.

The dosage administered depends upon the age, state of health and weight of the recipient, the extent of the disease, the nature of any other treatments to be given simultaneously, the frequency of the treatment and the nature of the desired action. Usually, the daily dosage of the active compound is from 0.1 to 50 mg/kg of body weight. Normally, 0.5 to 40 and preferably 1.0 to 20 mg/kg/day in one or more administrations per day are effective in order to achieve the desired results.

Apart from the compounds of formula I mentioned hereinafter in the Examples, as well as the esters and amides thereof, the following compounds are also preferred according to the present invention:

2-[(4-methylphenyl)-sulfonyl]-8-phenyloctanoic acid
2-[(4-methylphenyl)-sulfonyl]-5-phenylpent-4-ynoic acid
6-(4-methylphenyl)-2-[(4-methylphenyl)-sulfonyl]-hexanoic acid
7-(4-methylphenyl)-2-[(4-methylphenyl)-sulfonyl]-octanoic acid
8-(4-methylphenyl)-2-[(4-methylphenyl)-sulfonyl]-octanoic acid
10-(4-methylphenyl)-2-[(4-methylphenyl)-sulfonyl]decanoic acid
7-(4-chlorophenyl)-2-(amidosulfonyl)-heptanoic acid
7-(4-chlorophenyl)-2-(phenoxy)-heptanoic acid
7-(4-chlorophenyl)-2-(4-methylphenoxy)-heptanoic acid
7-(4-chlorophenyl)-2-(phenylthio)-heptanoic acid 7-(4-chlorophenyl)-2-(4-methylphenylthio)-heptanoic acid
7-(4-chlorophenyl)-2-(phenylsulfinyl)-heptanoic acid
7-(4-chlorophenyl)-2-(4-methylphenylsulfinyl)-heptanoic acid
6-(4-chlorophenyl)-2-[(4-methylphenyl)sulfonyl]hexanoic acid
7-(4-chlorophenyl)-2-(octylsulfonyl)-heptanoic acid
7-(4-chlorophenyl)-2-[(3-chlorophenylsulfonyl]heptanoic acid
7-(4-chlorophenyl)-2-[(4-methoxyphenyl)sulfonyl]heptanoic acid
7-(4-chlorophenyl)-2-[(3-trifluoromethylphenyl)sulfonyl]heptanoic acid
7-(4-chlorophenyl)-2-[(4-cyanophenyl)sulfonyl]heptanoic acid
7-(4-chlorophenyl)-2-[(4-nitrophenyl)sulfonyl]heptanoic acid
7-(4-chlorophenyl)-2-[(4-dimethylaminophenyl)sulfonyl]heptanoic acid
7-(4-chlorophenyl)-2-[(4-hydroxyphenyl)sulfonyl]heptanoic acid
7-(4-chlorophenyl)-2-[(4-acetylphenyl)sulfonyl]heptanoic acid
7-(4-chlorophenyl)-2-[(2-phenylethyl)sulfonyl]heptanoic acid
7-(4-chlorophenyl)-2-[(2-phenylethenyl)sulfonyl]heptanoic acid
7-(4-chlorophenyl)-2-[5-(4-chlorophenyl)-pentylsulfonyl]heptanoic acid
7-(4-chlorophenyl)-2-(naphth-1-ylsulfonyl)heptanoic acid
7-(4-chlorophenyl)-2-(naphth-2-ylsulfonyl)heptanoic acid
9-(4chlorophenyl)-2-[(4-methylphenyl)sulfonyl]-nonanoic acid
10-(4-chlorophenyl)-2-[(4-methylphenyl)sulfonyl-decanoic acid
7-(4-chlorophenyl)-2-[(4-methylphenyl)sulfonyl]-heptanoic acid
7-(4-chlorophenyl)-2-(phenylsulfonyl)-heptanoic acid
7-(4-chlorophenyl)-2-[(4-methylphenyl)sulfonyl]heptanoic acid
2-[(4-chlorophenyl)sulfonyl]-7-(4-methoxyphenyl)heptanoic acid
7-(4-methoxyphenyl)-2-[(4-methoxyphenyl)sulfonyl]-heptanoic acid
2-(phenylsulfonyl)-7-(3-trifluoromethylphenyl)heptanoic acid
2-[4-methylphenyl)sulfonyl]-7-(3-trifluoromethylphenyl)-heptanoic acid
2-[4-chlorophenyl)sulfonyl]-7-(3-trifluoromethylphenyl)-heptanoic acid
2-[(4-methoxyphenyl)sulfonyl]-7-(3-trifluoromethylphenyl)-heptanoic acid
7-(3,4-dichlorophenyl)-2-(phenylsulfonyl)-heptanoic acid
7-(3,4-dichlorophenyl)-2-[(4-methylphenyl)sulfonyl]-heptanoic acid
2-[(4-chlorophenyl)sulfonyl]-7-(3,4-dichlorophenyl)-heptanoic acid
7-(3,4-dichlorophenyl)-2-[(4-methoxyphenyl)sulfonyl]-heptanoic acid
2-[(4-methylphenyl)sulfonyl]-7-(naphth-1-yl)-heptanoic acid
2-[(4-methylphenyl)sulfonyl]-7-(naphth-2-yl)-heptanoic acid.

EXAMPLE 1

7-(4-chlorophenyl)-2-[(4-methylphenyl)sulfonyl]heptanoic acid (a) 9.69 g (40 mmol) of ethyl[(4-methylphenyl)sulfonyl]acetate is added at 50° C., with stirring, to a solution of 40 mmol of sodium ethylate in 55 ml of absolute ethanol. A suspension develops to which 10.46 g (40 mmol) of 5-(4-chlorophenyl)pentyl bromide is added, drop by drop, with heating at reflux temperature. The precipitate gradually passes into solution. Stirring of the reaction mixture is continued at reflux temperature, while new crystals gradually precipitate. After 5 hours, the reaction mixture is concentrated by evaporation, ice water is added to the residue, and the mixture is repeatedly extracted with acetic ester.

The combined organic phases are dried over sodium sulfate, concentrated, and the residue is chromatographed on silica gel with a mixture of chloroform and toluene (2:1).

Yield: 15.7 g (93% of theory) of ethyl 7-(4-chlorophenyl)-2-[(4-methylphenyl)sulfonyl]heptanoate, a colorless oil.

(b) A mixture of 4.2 g (9.9 mmol) of the above ethyl ester, 20 ml of 1N caustic potash and 125 ml of methanol is maintained for 2 h at 40° C. and then 20 ml of 1N hydrochloric acid is added. The methanol is then evaporated in vacuo and the aqueous residue is repeatedly extracted with methylene chloride. The combined organic extracts are dried over sodium sulfate and concentrated by evaporation. Yield: 3.05 g (78% of theory) of 7-(4-chlorophenyl)-2-[(4-methylphenyl)sulfonyl]heptanoic acid, a colorless oil.

The sodium salt is prepared by reaction with stoichiometric amounts of aqueous sodium hydrogen carbonate solution and concentration of the solution obtained. M.P. 90°–100° C. (amorphous).

Analogously to (a) and (b), [the following products] are obtained from ethyl [(4-methylphenyl)sulfonyl]acetate and:

3-(4-chlorophenyl)propyl bromide:
(a-1)
ethyl 5-(4-chlorophenyl)-2-[(4-methylphenyl)sulfonyl]pentanoate, a colorless oil, yield 87% of theory.
(b-1)
5-(4-chlorophenyl)-2-[(4-methylphenyl)sulfonyl]pentanic acid, sodium salt: M.P. 130° C. (decomposition), yield 63% of theory.

4-chlorocinnamyl chloride:
(a-2)
ethyl 5-(4-chlorophenyl)-2-[(4-methylphenyl)sulfonyl]-4-pentenoate, M.P. 87°–88° C., yield 46% of theory.
(b-2)
5-(4-chlorophenyl)-2-[(4-methylphenyl)sulfonyl]-4-pentenoic acid, M.P. 162°–164° C., yield 82% of theory.

4-(4-chlorophenoxy)butyl bromide:
(a-3)
ethyl 6-(4-chlorophenoxy)-2-[(4-methylphenyl)sulfonyl]hexanoate, a colorless oil, yield 67% of theory.
(b-3)
6-(4-chlorophenoxy)-2-[(4-methylphenyl)sulfonyl]-hexanoic acid, sodium salt: M.P. 168°–171° C., yield 82% of theory.

(a-4)
ethyl 8-(4-chlorophenyl)-2-[(4-methylphenyl)sulfonyl]octanoate, a colorless oil, yield 76% of theory.

(b-4)

8-(4-chlorophenyl)-2-[(4-methylphenyl)sulfonyl]octanoic acid, a colorless oil, yield 70% of theory.

5-phenylpentyl bromide:

(a-5)

ethyl 5-phenyl-2-[(4-methylphenyl)sulfonyl]heptanoate a colorless oil, yield 75% of theory.

(b-5)

5-phenyl-2-[(4-methylphenyl)sulfonyl]heptanoic acid, a colorless oil, yield 63% of theory.

EXAMPLE 2 ethyl 7-(4-chlorophenyl(-2[(4-methylphenyl)sulfonyloxy]-heptanoate (a) A solution of 1.84 g (48.6 mmol) of sodium hydroboride in 175 ml of ethanol is added rapidly, with stirring, to a solution of 11.25 g (44 mmol) of 7-(4-chlorophenyl)-2-oxoheptanoic acid in 175 ml of ethanol at 50° C. Then the mixture is let stand for 3 hours at room temperature, the reaction mixture is concentrated, and the residue is dissolved with water. After acidification the aqueous phase is extracted with acetic ester. The organic extracts are dried and concentrated. The residual oil is dissolved in aqueous sodium hydrogen carbonate solution, the solution is clarified with charcoal, and the oil that separates after acidification is dissolved with ether. By concentrating the dried ether solution, 7.4 g is obtained (65% of theory) of 7-(4-chlorophenyl)-2-hydroxyheptanoic acid, M.P. 78°–81° C.

(b) A mixture of 5.2 g (20.3 mmol) of the above alphahydroxycarboxylic acid, 1 g of Amerlite IR 120 (acid form) and 50 ml of absolute ethanol is heated at reflux temperature with stirring for 25 hours. Then it is aspirated from the ion exchanger resin and the filtrate is concentrated by evaporation. Yield: 5.7 g (quantitative) of ethyl 7-(4-chlorophenyl)-2-hydroxyheptanoate, a colorless oil.

(c) 13.4 g (70.2 mmol) of p-toluenesulfonyl chloride is added in portions over a period of 40 minutes to a solution of 10.0 g (35.1 mmol) of the above ethyl ester in 70 ml of dry pyridine, with stirring at 0° C. Then the mixture is let stand overnight under cool conditions, then poured onto ice, and the aqueous phase is extracted repeatedly with acetic ester. The combined acetic ester extracts are washed thrice with 1N hydrochloric acid, dried and concentrated. Yield: 13.0 g (84% of theory) of ethyl 7-(4-chlorophenyl)-2-[(4-methylphenyl)sulfonyloxy]heptanoate, colorless oil.

Analogously to (c), the following products are prepared from ethyl 7-(4-chlorophenyl)-2-(hydroxy)heptanoate:

(c-1) with methanesulfonyl chloride:

ethyl 7-(4-chlorophenyl)-2-(methylsulfonyloxy)heptanoate, colorless oil, yield 80% of theory.

(c-2) with benzenesulfonyl chloride ethyl 7-(4-chlorophenyl)-2-(phenylsulfonyloxy)heptanoate, colorless oil, yield 62% of theory.

(c-3) with 4-chlorobenzenesulfonyl chloride ethyl 7-(4-chlorophenyl)-2-[(4-chlorophenyl)sulfonyloxy]-heptanoate, colorless oil, yield 67% of theory.

EXAMPLE 3

Ethyl 7-(4-chlorophenyl)-2-methyl-2-[4-methylphenyl)sulfonyl-oxy]heptanoate (a) 29.3 mmol of a freshly prepared solution of methyl magnesium iodide in ether is added drop by drop to a solution of 8.3 g (29.3 mmol) of ethyl 7-(4-chlorophenyl)-2-oxoheptanoate in 60 ml of absolute ether, while stirring and cooling with ice. Then the cooling bath is removed and the mixture continues to be stirred for 2 hours at room temperature. Then the mixture is decomposed with sodium chloride solution, the organic phase is separated and dried and concentrated by evaporation. Yield: 7.05 g (80% of theory) of ethyl 7-(4-chlorophenyl)-2-hydroxy-2-methylheptanoate, colorless oil.

(b) To a solution of 7.05 g (23.6 mmol) of the above 2-hydroxycarboxylic acid ethyl ester in 100 ml of dry pyridine, 9.42 g (47.2 mmol) of p-toluenesulfonyl chloride is added in portions, with stirring at 0° C., and the reaction mixture is let stand overnight in the cold. Then it is poured onto ice, extracted with acetic ester, and the combined extracts are washed thrice with 1N hydrochloric acid. Then they are dried and concentrated by evaporation. The residue is chromatographed with a mixture of toluene and chloroform (1:1) on silica gel. Yield: 6.0 g (54% of theory) of ethyl 7-(4-chlorophenyl)-2-methyl-2-[(4-methyl-phenyl)sulfonyloxy]-heptanoate, colorless oil.

EXAMPLE 4

7-(4-chlorophenyl)-2-{[(4-methylphenyl)sulfonyl-]amino}heptanoic acid (a) 17.6 g (103 mmol) of ethyl acetaminocyanoacetate and 25.5 g (97.5 mmol) of 5-((4-chlorophenyl)-pentyl bromide are added to a solution of 2.46 g (107 mmol) of sodium in 100 ml of absolute ethanol, and the mixture is heated with stirring for 6 h at the reflux temperature. Then the ethanol is evaporated away, the residue is taken up in water, and adjusted ot pH 5 by the addition of a little dilute hydrochloric acid. Then it is extracted with acetic ester, the combined extracts are dried over sodium sulfate, and concentrated. The residue is taken up in a little ether and brought to crystallization in the cold. Yield: 16.0 g (47% of theory) of ethyl 2-acetamido-7-(4-chlorophenyl)-2-cyanoheptanoate, M.P. 73°–77° C.

(b) A mixture of the above ethyl ester, 16 g (45.6 mmol) of caustic soda and 160 ml of water is heated for 22 h at the refluxing temperature with stirring. Then it is adjusted to pH 6 with 6N hydrochloric acid and the precipitated crystals are removed with a suction filter in the cold. Yield: 11.3 g (97% of theory) of 7-(4-chlorophenyl)-2-aminoheptanoic acid, M.P. 218°-220° C.

(c) A mixture of 11.9 g (46.5 mmol) of the above amino acid and 120 ml of absolute ethanol is saturated with hydrogen chloride with ice cooling and then let stand overnight at room temperature. The reaction mixture is clarified with charcoal and the solution is concentrated by evaporation.

The residue is treated with ether and the crystals that form are removed on a suction filter in the cold. Yield: 8.6 g (58% of theory) of ethyl 7-(4-chlorophenyl)-2-aminoheptanoate hydrochloride, M.P. 101°–102° C.

(d) 2.85 g (14.9 mmol) of 4-toluensulfonic acid chloride is stirred in portions, at 0° C., into a solution of 4.35 g (13.6 mmol) of the above amino acid ester in 45 ml of dry pyridine. Stirring is continued for 3 h with ice cooling; the reaction mixture is then poured onto ice and acidified with concentrated hydrochloric acid. The aqueous phase is extracted with ether and the ether extracts are washed twice with 0.5N hydrochloric acid. Then the solution is dried, decolored with charcoal, and concentrated. The concentrate is brought to crystallization by grinding it under ligroin. Yield: 3.6 g (60% of theory) of ethyl 7-(4-chlorophenyl)-2-[(4-methylphenyl)sulfonylamino]heptanoate, M.P. 56°-58° C.

(e) A mixture of 4.0 g (9.1 mmol) of the above sulfonated amino esters, 23 ml of 1N potash lye and 55 ml of methanol is stirred at 40° C. for 6 hours. The solution is then clarified with charcoal, acidified with 23 ml of 1N hydrochloric acid, diluted with water and the precipitated oil is taken up in acetic ester. The acetic ester solution is dried and concentrated. The concentrate is brought to crystallization under ligroin. Yield: 2.6 g (70% of theory) of 7-(4-chlorophenyl)-2-[(4-methylphenyl)sulfonylamino]heptanic acid, M.P. 88°-90° C.

Analogously to (d) and (e), the following products were prepared from ethyl 7-(4-chlorophenyl)-2-aminoheptanoate hydrochloride and methanesulfonyl chloride:

(d-1)
ethyl 7-(4-chlorophenyl)-2-[(methylsulfonyl)amino]-heptanoate, M.P. 60°-62° C., yield 68% of theory.
(e-1)
7-(4-chlorophenyl)-2-[(methylsulfonyl)amino]heptanoic acid, M.P. 73°-75° C., yield 82% of theory.

EXAMPLE 5

Ethyl 7-(4-chlorophenyl)-2-[(4-chlorophenyl)sulfonyl]heptanoate

By the procedure described in Example 1(a), 9.3 g (52% of theory) of ethyl 7-(4-chlorophenyl)-2-[(4-chlorophenyl)sulfonyl]heptanoate, a colorless oil, is obtained from 40 mmol of sodium ethylate, 10.51 g (40 mmol) of ethyl (4-chlorophenyl)-sulfonylacetate and 10.46 g (40 mmol) of 5-(4-chlorophenyl)pentyl bromide in 100 ml of absolute ethanol.

By an analogous method, the following products are obtained from 5-(4-chlorophenyl)pentyl bromide and (a) ethyl trifluoromethylsulfonylacetate: ethyl 5-(4-chlorophenyl)-2-(trifluoromethylsulfonyl)-heptanoate, a colorless oil, yield 56% of theory.

(b) ethyl methylsulfonylacetate: ethyl 5-(4-chlorophenyl)-2-(methylsulfonyl)heptanoate, M.P. 60°-62° C., yield 64% of theory.

(c) ethyl phenylsulfonylacetate: ethyl 5-(4-chlorophenyl)-2-(phenylsulfonyl)heptanoate, a colorless oil, yield 77% of theory.

(d) ethyl 2-[(4-methylphenyl)sulfonyl]propionate: ethyl 5-(4-chlorophenyl)-2-methyl-2-[(4-methylphenyl)sulfonyl]heptanoate, colorless oil, yield 74% of theory.

EXAMPLE 6

7-(4-chlorophenyl)-2-[(4-chlorophenyl)sulfonyl]heptanoic acid

By the procedure described in Example 1(b), 5.1 g (75% of theory) of the sodium salt of 7-(4-chlorophenyl)-2-[(4-chlorophenyl)sulfonyl]heptanoic acid, amorphous powder, is obtained from 6.9 g (15.6 mmol) of ethyl 7-(4-chlorophenyl)-2-[(4-chlorophenyl)sulfonyl]-heptanoate (Example 5) and 34 ml of 1N potash lye in 100 ml of methanol.

Analogously, the following are obtained from (a) ethyl 7-(4-chlorophenyl)-2-(methylsulfonyl)heptanoate (Example 5b): 7-(4-chlorophenyl)-2-(methylsulfonyl)heptanoic acid, M.P. 81°-84° C., yield 85% of theory.

(b) ethyl 7-(4-chlorophenyl)-2-(phenylsulonyl)heptanoate (Example 5c): 7-(4-chlorophenyl)-2-(phenylsulfonyl)heptanoic acid, M.P. 95°-97° C., yield 71% of theory.

(c) 7-(4-chlorophenyl)-2-methyl-2-[(4-methylphenyl)sulfonyl]heptanoic acid, colorless oil, yield 62% of theory.

EXAMPLE 7

Ethyl 5-(4-chlorophenyl)-2-[3-(4-chlorophenyl)-2-propenyl]-2-[(4-methylphenyl)sulfonyl]pentan-4-oate 4.35 g (20 mmol) of ethyl (4-methylphenyl)sulfonyl acetate is added with stirring to a solution of 40 mmol of sodium ethylate in 100 ml of absolute ethanol at 60° C.

The reaction is allowed to go to completion for 15 minutes and 7.48 g (40 mmol) of 4-chlorocinnamyl chloride is added to the precipitate that forms. The reaction mixture is then heated to reflux temperature for 5 hours, concentrated, and the concentrate is treated with ether. The ether solution is washed with water, dried and concentrated. The concentrate is chromatographed with toluene on silica gel. 13.4 g (62% theory) is obtained of the title compound, M.P. 75°-78° C.

EXAMPLE 8

7-(4-chlorophenyl)-2-[(4-methylphenyl)sulfonyl]heptane nitrile

A mixture of 4.5 g (17.2 mmol) of 5-(4-chlorophenyl)-pentyl bromide, 3.36 g (17.2 mmol) of (4-methylphenyl)sulfonylacetonitrile, 2.26 g (17.2 mmol) of 1,8-diazabicyclo(5,4,0)undec-7-ene and 30 ml of benzene is stirred at room temperature for 6 hours. Then the reaction mixture is washed with water; the organic phase is dried, and concentrated. The concentrate is chromatographed with a mixture of toluene and dioxane (10:1) on silica gel. Yield: 4.2 g (65% of theory) of the title compound, a colorless oil.

EXAMPLE 9

7-(4-chlorophenyl)-2-2(4-methylphenoxy)pentanoic acid (a) 8.1 g (0.186 mol) of 55% sodium hydride in a mineral oil suspension is added in portions to a solution of 63.4 g (0.186 mol) of ethyl 7-(4-chlorophenyl)-2-ethoxycarbonylheptanoate (BM 13.861) in 500 ml of absolute tetrahydrofuran, and stirred for another 15 minutes to complete the salt formation. Then 33.1 g (0.186 mol) of N-bromosuccinimide is added and the mixture is stirred for 8 h at room temperature. Then it is poured into water, acidified, and extracted with ether. The combined extracts are washed, dried and concentrated by evaporation. The concentrate is chromatograhied with toluene on silica gel. 61.3 g (78% of theory) of ethyl 2-bromo-7-(4-chlorophenyl)-2-ethoxycarbonylheptanoate, a colorless oil, is obtained.

(b) A mixture of 102.7 g (0.245 mol) of ethyl 2-bromo-7-(4-chlorophenyl)-2-ethoxycarbonylheptanoate, 367 ml of acetic acid and 367 ml of 6N hydrobromic acid is heated at refluxing temperature for 60 hours. Then it is diluted with water and extracted with ether. The extracts are clarified with charcoal, dried and concentrated by evaporation.

The concentrate is ground with ligroin. 67.8 g (86% of theory) of 2-bromo-7-(4-chlorophenyl)heptanoic acid is obtained, M.P. 77°–79° C.

(c) To a solution of 31.0 g (0.097 mol) of 2-bromo-7-(4-chlorophenyl)heptanoic acid in 250 ml of absolute ether which contains 0.5 ml of methanol, a solution of about 0.16 mol of diazomethane in 300 ml of absolute ether is added drop by drop, with stirring, at room temperature, until the evolution of nitrogen ceases. Then the reaction mixture is concentrated by evaporation and the concentrate is chromatographed with toluene on silica gel. 18.1 g (56% of theory) is obtained of ethyl 2-bromo-7-(4-chlorophenyl)heptanoate, a colorless oil.

(d) A mixture of 5.6 g (17 mmol) of ethyl 2-bromo-7-(4-chloro-phenyl)heptanoate, 1.82 g (17 mmol) of p-cresol, 7.0 g (50 mmol) of potassium carbonate and 70 ml of butanone is heated for 36 h at the refluxing temperature. Then the inorganic precipitate is removed on a suction filter and the filtrate is concentrated. The residue is taken up in ether, the solution washed twice with 0.5N caustic soda solution, dried and concentrated by evaporation. The residual oil is chromatographed with toluene on silica gel. 5.3 g (86% of theory) is obtained of ethyl 7-(4-chloro-phenyl)-2-(4-methylphenoxy)heptanoate, a colorless oil.

(e) A mixture of 3.25 g (9 mmol) of ethyl 7-(4-chlorophenyl)-2-(4-methylphenoxy)heptanoate, 15 ml of 1N caustic potash solution and 45 ml of methanol is heated for 3 h, with stirring, at 40° C. Then the methanol is evaporated in vacuo, the aqueous solution is washed with ether and acidified with dilute hydrochloric acid. The precipitated oil is taken up in ether and the ether solution is dried and concentrated by evaporation. The residue is ground with ligroin. 2.7 g (86% of theory) is obtained of 7-(4-chlorophenyl)-2-(4-methylphenoxy)-heptanoic acid, M.P. 74°–76° C.

EXAMPLE 10

Methyl 7-(4-chlorophenyl)-2-(4-methylphenylthio)heptanoate

By the procedure described in Example 9(d), 3.7 g (54% of theory) is obtained of methyl 7-(4-chlorophenyl)-2-(4-methylphenylthio)heptanoate, a colorless oil, is obtained from 6.0 g (18 mmol) of methyl 2-bromo-7-(4-chlorophenyl)-2-(4-methylphenylthio)heptanoate, 2.23 g (18 mmol) of p-thiocresol, 7.4 g (54 mmol) of potassium carbonate and 75 ml of butanone.

EXAMPLE 11

7-(4-chlorophenyl)-2-(4-methylphenylthio)heptanoic acid

A solution of 2.12 g (53 mmol) of caustic soda in 5 ml of water is added under nitrogen, at 0° C., to a solution of 3.27 g (26.3 mmol) of p-thiocresol in 50 ml of ethanol. Then a solution of 8.4 g (26.3 mmol) of 2-bromo-7-(4-chlorophenyl)heptanoic acid in 5 ml of ethanol is added and the cooling bath is removed. Then stirring is continued for 6 at room temperature; the mixture is let stand overnight and concentrated by evaporation. The residue is taken up in water, washed with ether and acidified with hydrochloric acid. The precipitated oil is extracted with methylene chloride. The extracts are dried and concentrated. The concentrate is chromatographed with a mixture of toluene and dioxane (5:1) on silica gel. Yield: 6.6 g (69% of theory) of 7-(4-chlorophenyl)-2-(4-methylphenylthio)heptanoic acid, M.P. 58°–61° C.

EXAMPLE 12

Ethyl 7-(4-chlorophenyl)-2-[(4-methylphenyl)sulfinyl]heptanoate

First 1.64 g (37.6 mmol) of sodium hydride in 55% mineral oil suspension, and then 9.8 g (37.6 mmol) of 5-(4-chlorophenyl)pentyl bromide, are added to a solution of 8.5 g (37.6 mmol) of ethyl 4-methylphenylsulfinylacetate in 75 ml of dimethylsulfoxide. Then the mixture is stirred at room temperature for another 4 hours. Then it is poured into water, extracted with ether, the extracts are washed with water, dried and concentrated. The concentrate is chromatographed with a mixture of n-heptane and butanone (2:1) on silica gel. Yield: 8.0 g (52% of theory) of ethyl 7-(4-chlorophenyl)-2-[(4-methylphenyl)sulfinyl]heptanoate, a colorless oil.

EXAMPLE 13

Ethyl 2-[(4-methylphenyl)sulfonyl]octanoate

By the procedure described in Example 1(a), 7.3 g (56% of theory) of ethyl 2-[(4-methylphenyl)sulfonyl]octanoate, a colorless oil, is obtained from 40 mmol of sodium ethylate, 9.7 g (40 mmol) of ethyl (4-methylphenyl)sulfonylacetate and 7.26 g (44 mmol) of n-hexyl bromide in 100 ml of ethanol.

Analogously, the following are obtained from (4-methylphenyl)sulfonylacetate and (a) n-octyl bromide: ethyl 2-[(4-methylphenyl)sulfonyl]decanoate, a colorless oil, yield 52% of theory.

The methyl ester of the acid in question has already been described as a colorless oil by Ono et al., Bull. Chem. Soc. Jpn. 1979, 52, 1716.

(b) n-decyl bromide: ethyl 2-[(4-methylphenyl)sulfonyl]dodecanoate, a colorless oil, yield 57% of theory.

(c) n-tetradecyl bromide: ethyl 2-[(4-methylphenyl)sulfonyl]hexadecanoate, M.P. 38°–40° C., yield 68% of theory.

The methyl ester of the acid in question has already been described by Engel and Cowburn, J. Biomol. Struct. Dyn. 1983, 1, 319.

EXAMPLE 14

2-[(4-methylphenyl)sulfonyl]octanoic acid

By the procedure described in Example 1(b), 2.6 g (60% of theory) of 2-[(4-methylphenyl)sulfonyl]octanoic acid, MP 111°–123° C. (acetic acid ethyl ester), is obtained from 4.75 g (14.5 mmol) of ethyl 2-[(4-methylphenyl)sulfonyl]octanoate (Example 13) and 32 ml of 1N potash lye.

Analogously, the following are obtained from (a) ethyl 2-[(4-methylphenyl)sulfonyl]decanoate (Example 13a): 2-[(4-methylphenyl)sulfonyl]decanoic acid, M.P. 116°–118° C., yield 77% of theory.

(b) ethyl 2-[(4-methylphenyl)sulfonyl]dodecanoate (Example 13b): 2-[(4-methylphenyl)sulfonyl]dodecanoic acid, M.P. 71°–73° C. (ligroin) yield 92% of theory.

This compound has already been described by Takur and Nargund, Indian J. Chem., Sect. B 1977, 15 B, 287, as a potential tuberculostatic.

(c) ethyl 2-[(4-methylphenyl)sulfonyl]hexadecanoate (Example 13c): 2-[(4-methylphenyl)sulfonyl]hexadecanoic acid, M.P. 87°-90° C., yield 93% of theory.

EXAMPLE 15

2-[(4-methylphenyl)sulfonyl]-4-methyl-5-phenylpent-4-enoic acid

By the procedure described in Example 1(a), the following are obtained from 9.69 g (40 mmol) of ethyl (4-methylphenyl)sulfonylacetate, 40 mmol of sodium ethylate and 6.66 g (40 mmol) of 2-methyl-3-phenyl-2-pentenyl chloride in 100 ml of absolute ethanol: 8.2 g (55% of theory) of ethyl 2-[(4-methylphenyl)sulfonyl]-4-methyl-5-phenylpent-4-enoate, M.P. 123°-124° C. (ethyl acetate/ligroin) BM 13,889, and from that, by the procedure described in Example 1(b), 6.8 g (90% of theory) of 2-[(4-methylphenyl)sulfonyl]-4-methyl-5-phenyl-4-pentenoic acid, sticky crystals. The sodium salt melts at 140°-142° C.

Analogously, the following are obtained from (a) ethyl (4-methylphenyl)sulfonylacetate and 5-phenyl-4-pentenyl bromide: ethyl 2-[(4-methylphenyl)sulfonyl]-7-phenyl-6-heptenoate, M.P. 46°-49° C., yield 56%, and from this: 2-[(4-methylphenyl)sulfonyl]-7-phenyl-6-heptenoic acid, colorless oil, yield 75%, sodium salt: M.P. 144° C. (decomposition).

(b) ethyl (4-methylphenyl)sulfonylacetate and 5-(4-methylphenyl)pentyl bromide: ethyl 2-[(4-methylphenyl)sulfonyl]-7-(4-methylphenyl)-heptanoate, colorless oil, yield 67%, and from this: 2-[(4-methylphenyl)sulfonyl]-7-(4-methylphenyl)heptanoic acid, colorless oil, yield 83%.

(c) ethyl (4-methylphenyl)sulfonylacetate and 4-(4-chlorophenyl)butyl bromide: ethyl 6-(4-chlorophenyl)-2-[(4-methylphenyl)sulfonyl]acetate, colorless oil, yield 74%, and from this: 6-(4-chlorophenyl)-2-[(4-methylphenyl)sulfonyl]hexanoic acid, colorless oil, yield 99%, sodium salt: M.P. 143°-145° C.

(d) ethyl (3-chlorophenyl)sulfonylacetate and 4-(4-chlorophenyl)pentyl bromide: ethyl 7-(4-chlorophenyl)-2-[(3-chlorophenyl)sulfonyl]heptanoate, colorless oil, yield 69%, and from this: 7-(4-chlorophenyl)-2-[(3-chlorophenyl)sulfonyl]heptanoic acid, M.P. 104°-106° C., yield 73%.

(e) ethyl (4-methoxyphenyl)sulfonylacetate and 5-(4-chlorophenyl)pentyl bromide: ethyl 7-(4-chlorophenyl)-2-[(4-methoxyphenyl)sulfonyl]heptanoate, colorless oil, yield 79%, and from this: 7-(4-chlorophenyl)-2-[(4-methoxyphenyl)sulfonyl]heptanoic acid, M.P. 58°-65° C., yield 64%.

(f) ethyl (3-trifluoromethylphenyl)sulfonylacetate and 5-(4-chlorophenyl)pentyl bromide: ethyl 7-(4-chlorophenyl)-2-[(3-trifluoromethylphenyl)sulfonyl]heptanoate, colorless oil, yield 52%, and from this: 7-(4-chlorophenyl)-2-[(3-trifluoromethylphenyl)sulfonyl]heptanoic acid, M.P. 107°-108° C., yield 73%, sodium salt: M.P. 147°-150° C.

(g) ethyl (4-cyanophenyl)sulfonylacetate and 5-(4-chlorophenyl)pentyl bromide: ethyl 7-(4-chlorophenyl)-2-[(4-cyanophenyl)sulfonyl]heptanoate, colorless oil, yield 65%.

(h) ethyl (4-acetylphenyl)sulfonylacetate and 5-(4-chlorophenyl)pentyl bromide: ethyl 2-[(4-acetylphenyl)sulfonyl]-7-(4-chlorophenyl)-heptanoate, colorless oil, yield 54%.

(i) ethyl (1-naphthyl)sulfonylacetate and 5-(4-chlorophenyl)pentyl bromide: ethyl 7-(4-chlorophenyl)-2-[(1-naphthyl)sulfonyl]heptanoate, colorless oil, yield 71%, and from this 7-(4-chlorophenyl)-2-[(1-naphthyl)sulfonyl]heptanoic acid, colorless oil, yield 63%, sodium salt: M.P. 168°-170° C.

(j) ethyl (4-methylphenyl)sulfonylacetate and 6-(4-chlorophenyl)hexyl bromide: ethyl 8-(4-chlorophenyl)-2-[(4-methylphenyl)sulfonyl]octanoate, colorless oil, yield 67%, and from this: 8-(4-chlorophenyl)-2-[(4-methylphenyl)sulfonyl]octanoic acid, colorless oil, yield 71%.

(k) ethyl (4-methylphenyl)sulfonylacetate and 4-(4-chlorophenoxy)butyl bromide: ethyl 6-(4-chlorophenoxy)-2-[(4-methylphenyl)sulfonyl]hexanoate, colorless oil, yield 67%, and from this: 6-(4-chlorophenoxy)-2-[(4-methylphenyl)sulfonyl]hexanoic acid, colorless oil, yield 82%, sodium salt: M.P. 168°-171° C.

(l) ethyl (4-methylphenyl)sulfonylacetate and 5-(4-chlorophenoxy)pentyl bromide: ethyl 7-(4-chlorophenoxy)-2-[(4-methylphenyl)sulfonyl]heptanoate. M.P. 86°-89° C., yield 63%, and from this: 7-(4-chlorophenoxy)-2-[(4-methylphenyl)sulfonyl]heptanoic acid, M.P. 88°-90° C., yield 87%.

(m) ethyl (4-methylphenyl)sulfonylacetate and 5-(4-methoxyphenyl)pentyl bromide: ethyl 7-(4-methoxyphenyl)-2-[(4-methylphenyl)sulfonyl]heptanoate, M.P. 64°-68° C., yield 56%, and from this: 7-(4-methoxyphenyl)-2-[(4-methylphenyl)sulfonyl]heptanoic acid, colorless oil, yield 70%, sodium salt: M.P. 72°-80° C. (decomposition).

(n) ethyl (4-methylphenyl)sulfonylacetate and 5-(3-trifluoromethylphenyl)pentyl bromide: ethyl 2-[(4-methylphenyl)sulfonyl]-7-(3-trifluoromethylphenyl)-heptanoate, M.P. 56°-58° C., yield 53%, and from this: 2-[(4-methylphenyl)sulfonyl]-7-(3-trifluoromethylphenyl)heptanoic acid, M.P. 62° C., yield 87%.

(o) ethyl (4-methylphenyl)sulfonylacetate and 5-(2-methoxyphenyl)pentyl bromide: ethyl 7-(2-methoxyphenyl)-2-[(4-methylphenyl)sulfonyl]heptanoate, colorless oil, yield 64%, and from this: 7-(2-methoxyphenyl)-2-[(4-methylphenyl)sulfonyl]heptanoic acid, colorless oil, yield 70%, sodium salt: M.P. 65°-76° C.

(p) ethyl (4-methylphenyl)sulfonylacetate and 5-(3-methoxyphenyl)pentyl bromide: ethyl 7-(3-methoxyphenyl)-2-[(4-methylphenyl)sulfonyl]heptanoate, colorless oil, yield 52%, and from this: 7-(3-methoxyphenyl)-2-[(4-methoxyphenyl)sulfonyl]heptanoic acid, colorless oil, yield 60%, sodium salt: M.P. 84°-85° C.

(q) ethyl (4-methylphenyl)sulfonylacetate and 3-(4-chlorophenyl)-2-propine bromide: ethyl 5-(4-chlorophenyl)-2-[(4-methylphenyl)sulfonyl]pent-4-ynoate, M.P. 78°-79° C., yield 57%, and from this: 5-(4-chlorophenyl)-2-[(4-methylphenyl)sulfonyl]-pent-4-ynoic acid, M.P. 154°-157° C., yield 76%.

EXAMPLE 16

2-(aminocarbonyl)-7-(4-chlorophenyl)heptanoic acid (a) A solution of 3.9 g (34.4 mmol) of ethyl cyanoacetate in 36 ml of anhydrous benzene is added to a mixture of 9.0 g (34.4 mmol) of 1,8-diazabicyclo(5,4,0)-undec-7-ene and 18 ml of anhydrous benzene, with stirring, and the mixture is then stirred for another 16 h at room temperature. Then the organic phase is washed with water, dried and concentrated. The concentrate is chromatographed on silica gel with a mixture of n-heptane and butanone (2:1). 8.8 g (87% of theory) of ethyl 7-(4-chlorophenyl)-2-cyanoheptanoate, colorless oil, is obtained.

(b) 12 g (41 mmol) of ethyl 7-(4-chlorophenyl)-2-cyanoheptanoate and 96 g of polyphosphoric acid are heated for 3 hours at 100° C. with stirring. Then the mixture is diluted with 200 ml of water and extracted thrice with methylene chloride. The combined extracts are washed with water, dried and concentrated. 10 g (78% of theory) of ethyl 2-(aminocarbonyl)-7-(4-chlorophenyl)heptanoate is obtained, M.P. 110°–111° C.

(c) A mixture of 7.8 g (25 mmol) of ethyl 2-(aminocarbonyl)-4-(4-chlorophenyl)heptanoate, 25 ml of 1N potash lye and 100 ml of methanol are stirred for 4 h at 40° C. Then the methanol is evaporated away, the residue is treated with charcoal, and it is acidified with 2N hydrochloric acid. The separated crude acid is extracted with methylene chloride, and the extracts are dried, and concentrated. The concentrate is recrystallized out of a mixture of acetic ester and ligroin. Yield: 4.8 g (68% of theory) of 2-(aminocarbonyl)-7-(4-chlorophenyl)heptanoic acid, M.P. 125°–126° C.

Analogously, the following are obtained from 3-(4-chlorophenyl)propyl bromide and ethyl cyanoacetate
(a-1) ethyl 5-(4-chlorophenyl)-2-cyanopentanoate, colorless oil, yield 74% of theory.
(b-1) ethyl 2-(aminocarbonyl)-5-(4-chlorophenyl)pentanoate M.P. 99°–101° C. (acetic ester/ligroin).
from 6-(4-chlorophenyl)hexyl bromide and ethyl cyanoacetate
(a-2) ethyl 8-(4-chlorophenyl)-2-cyanooctanoate, colorless oil, yield 87% of theory.
(b-2) ethyl 2-(aminocarbonyl)-8-(4-chlorophenyl)octanoate, M.P. 121°–122° C. (acetic ester/ligroin).

EXAMPLE 17

Ethyl 2-acetyl-7-(4-chlorophenyl)heptanoate

A solution of 6.0 g (46 mmol) of ethyl acetoacetate in 6 ml of absolute ethanol is added drop by drop, with stirring, to a solution of 23 mmol of sodium ethylate in 18 ml of ethanol. Stirring is continued for another 15 minutes to complete the salt formation, and then a solution of 6.0 g (23 mmol) of 5-(4-chlorophenyl)pentyl bromide in 6 ml of absolute ethanol is added. The mixture is then heated for 3 hours with refluxing, and then completely concentrated by evaporation. Water is added to the concentrate and the mixture is neutralized with 2N hydrochloric acid. Then the organic components are extracted with ether, the combined extracts are dried, and are concentrated by evaporation. The concentrate is chromatographed on silica gel with a mixture of n-heptane and butanone. Yield: 5.8 g (81% of theory) of ethyl 2-acetyl-7-(4-chlorophenyl)heptanoate, a colorless oil.

EXAMPLE 18

5-(4-chlorophenyl)-2-[3-(4-chlorophenyl)-2-prop-2-yn-1-yl]-2-(4-methylphenylsulfonyl)-pent-4-ynoate By the procedure described in Example 1 (a), 8.1 g (44% of theory) of the title compound is obtained from 7.8 g (34 mmol) of ethyl (4-methylphenyl)-sulfonylacetate, 68 mmol of sodium ethylate and 16.5 g (68 mmol) of 3-(4-chlorophenyl)-prop-2-yn-1-yl bromide; M.P. 90°–93° C.

EXAMPLE 19

Ethyl 2-(aminocarbonyl)-7-(4-chlorophenyl)heptanoate

A saturated solution of gaseous ammonia in 25 ml of methylene chloride is added drop by drop at −10° C. to a solution of 5.6 (17 mmol) of ethyl 2-(chlorocarbonyl)-7-(4-chlorophenyl)heptanoate in 50 ml of methylene chloride. The mixture is stirred for 30 minutes at room temperature, suction filtered from the ammonium chloride, the filtrate is washed with water, and dried and concentrated. The concentrate is chromatographed on silica gel with a mixture of toluene and dioxane (5:1). 3.6 g (68% of theory) is obtained of ethyl 2-(aminocarbonyl)-7-(4-chlorophenyl)heptanoate, M.P. 110°–111° C.

EXAMPLE 20

By the appropriate selection of starting components and reaction conditions the following can be produced analogously to the foregoing examples:
7-(4-chlorophenyl)-2-(methoxy)heptanoic acid
7-(4-chlorophenyl)-2-(methylthio)heptanoic acid
7-(4-chlorophenyl)-2-(methylsulfoxyl)heptanoic acid
7-(4-chlorophenyl)-2-(phenoxy)heptanoic acid
7-(4-chlorophenyl)-2-(4-chlorophenoxy)heptanoic acid
7-(4-chlorophenyl)-2-(4-methoxyphenoxy)heptanoic acid
7-(4-chlorophenyl)-2-(3-trifluoromethylphenoxy)heptanoic acid
7-(4-chlorophenyl)-2-(4-cyanophenoxy)heptanoic acid
2-(4-methoxyphenoxy)-7-phenylheptanoic acid
7-(4-methoxyphenyl)-2-(4-methylphenoxy)heptanoic acid
2-(4-methylphenoxy)-7-(3-trifluoromethylphenyl)-heptanoic acid
7-(4-chlorophenyl)-2-phenylthioheptanoic acid
7-(4-chlorophenyl)-2-(4-chlorophenylthio)-heptanoic acid
7-(4-chlorophenyl)-2-(4-methoxyphenylthio)-heptanoic acid
7-(4-chlorophenyl)-2-(3-trifluoromethylphenylthio)-heptanoic acid
7-(4-chlorophenyl)-2-(4-cyanophenylthio)-heptanoic acid
2-(4-methylphenyl)-thio-7-phenylheptanoic acid
7-(4-methoxyphenyl)-2-(4-methylphenylthio)-heptanoic acid
2-(4-methylphenyl)-thio-7-(3-trifluoromethylphenyl)-heptanoic acid
7-(4-chlorophenyl-2-phenylsulfinylheptanoic acid
7-(4-chlorophenyl)-2-(4-chlorophenylsulfinyl)-heptanoic acid
7-(4-chlorophenyl)-2-(4-methoxyphenylsulfinyl)-heptanoic acid
7-(4-chlorophenyl)-2-(3-trifluoromethylphenylsulfinyl)-heptanoic acid
7-(4-chlorophenyl)-2-(4-cyanophenylsulfinyl)-heptanoic acid
2-(4-methylphenylsulfinyl)-7-phenylheptanoic acid
7-(4-methoxyphenyl)-2-(4-methylphenylsulfinyl)-heptanoic acid
2-(4-methylphenyl)-sulfinyl-7-(3-trifluoromethylphenyl)-heptanoic acid
6-cyclohexyl-2-(4-methylphenylsulfonyl)-hexanoic acid
8-cyclohexyl-2-(4-methylphenylsulfonyl)-octanoic acid
8-methoxy-2-(4-methylphenylsulfonyl)-octanoic acid
8-methylthio-2-(4-methylphenylsulfonyl)-octanoic acid
8-methylsulfinyl-2-(4-methylphenylsulfonyl)-octanoic acid
4-methyl-2-(4-methylphenylsulfonyl)-5-phenylpentanoic acid
2-(4-methylphenylsulfonyl)-5-phenylpent-4-ynoic acid 2-(4-methylphenylsulfonyl)-6-phenylhexanoic acid
7-phenyl-2-(phenylsulfonyl)-heptanoic acid
2-(4-chlorophenylsulfonyl)-7-phenylheptanoic acid
2-(4-methoxyphenylsulfonyl)-7-phenylheptanoic acid
2-(4-cyanophenylsulfonyl)-7-phenylheptanoic acid
7-phenyl-2-(3-trifluoromethylphenylsulfonyl)-heptanoic acid
7,7-dimethyl-2-(4-methylphenylsulfonyl)-7-phenyl-heptanoic acid
2-(4-methylphenylsulfonyl)-8-phenyloctanoic acid
6-(4-methylphenyl)-2-(4-methylphenylsulfonyl)hexanoic acid
8-(4-methylphenyl)-2-(4-methylphenylsulfonyl)-octanoic acid
10-(4-methylphenyl)-2-(4-methylphenylsulfonyl)-decanoic acid
7-(4-chlorophenyl)-2-(octylsulfonyl)-heptanoic acid
7-(4-chlorophenyl)-2-(4-nitrophenylsulfonyl)-heptanoic acid
7-(4-chlorophenyl)-2-(4-dimethylaminophenylsulfonyl)-heptanoic acid
7-(4-chlorophenyl)-2-(4-hydroxyphenylsulfonyl)-heptanoic acid
7-(4-chlorophenyl)2-(2-naphthylsulfonyl)-heptanoic acid
9-(4-chlorophenyl)-2-(4-methylphenylsulfonyl)-nonanoic acid
10-(4-chlorophenyl)-2-(4-methylphenylsulfonyl)-decanoic acid
7-(4-chlorophenyl)-2-(2-phenylethylsulfonyl)heptanoic acid
7-(4-chlorophenyl)-2-(2-phenylethenylsulfonyl)-heptanoic acid
7-(4-chlorophenyl)-2-(4-methylphenylsulfonyl)-hept-6-enoic acid
5-(4-methoxyphenyl)-2-(4-methylphenylsulfonyl)-pent-4-ynoic acid
2-(4-methylphenylsulfonyl)-5-(3-trifluoromethylphenyl)-pent-4-ynoic acid
5-(4-chlorophenyl)-2-(phenylsulfonyl)-pent-4-ynoic acid
5-(4-chlorophenyl)-2-(4-chlorophenylsulfonyl)-pent-4-ynoic acid
5-(4-chlorophenyl)-2-(3-trifluoromethylphenylsulfonyl)-pent-4-ynoic acid
5-4-chlorophenyl)-2-(4-methoxyphenylsulfonyl)-pent-4-ynoic acid
5-(4-chlorophenyl)-2-(4-cyanophenylsulfonyl)-pent-4-ynoic acid
7-(4-methosyphenyl)-2-(phenylsulfonyl)-heptanoic acid
2-(4-chlorophenylsulfonyl)-7-(4-methoxyphenyl)-heptanoic acid
7-(4-methoxyphenyl)-2-(4-methoxyphenylsulfonyl)-heptanoic acid
2-(phenylsulfonyl)-7-(3-trifluoromethylphenyl)-heptanoic acid
2-(4-chlorophenylsulfonyl)-7-(3-trifluoromethylphenyl)-heptanoic acid
2-(4-methoxyphenylsulfonyl)-7-(3-trifluoromethylphenyl)-heptanoic acid
7-(3,4-dichlorophenyl)-2-(phenylsulfonyl)-heptanoic acid
7-(3,4-dichlorophenyl)-2-(4-methylphenylsulfonyl)-heptanoic acid
2-(4-chlorophenylsulfonyl)-7-(3,4-dichlorophenyl)-heptanoic acid
7-(3,4-dichlorophenyl)-2-(4-methoxyphenylsulfonyl)-heptanoic acid
7-(4-fluorophenyl)-2-(4-methylphenylsulfonyl)-heptanoic acid
7-(3-chlorophenyl)-2-(4-methylphenylsulfonyl)-heptanoic acid
7-(4-aminophenyl)-2-(4-methylphenylsulfonyl)-heptanoic acid
2-(4-methylphenylsulfonyl)-7-(4-nitrophenyl)-heptanoic acid
2-(4-methylphenylsulfonyl)-7-(1-naphthyl)-heptanoic acid
2-(4-methylphenylsulfonyl)-7-(2-naphthyl)-heptanoic acid
2-acetoxy-7-(4-chlorophenyl)-heptanoic acid
2-benzoyloxy-7-(4-chlorophenyl)-heptanoic acid
2-amino-7-(4-chlorophenyl)-heptanoic acid
2-amino-8-(4-chlorophenyl)-octanoic acid
2-amino-7-(4-methoxyphenyl)-heptanoic acid
2-amino-7-(3-trifluoromethylphenyl)-heptanoic acid
2-acetylamino-7-(4-chlorophenyl)-heptanoic acid
2-(benzoylamino)-7-(4-chlorophenyl)-heptanoic acid
7-(4-chlorophenyl)-2-phenylaminoheptanoic acid
2-benzylamino-7-(4-chlorophenyl)-heptanoic acid
7-(4-chlorophenyl)-2-piperidinoheptanoic acid
7-(4-chlorophenyl)-2-morpholinoheptanoic acid
7-(4-chlorophenyl)-2-(4-phenylpiperazino)-heptanoic acid
2-aminosulfonyl-7-(4-chlorophenyl)-heptanoic acid
7-(4-chlorophenyl)-2-(diethylaminosulfonyl)-heptanoic acid
7-(4-chlorophenyl)-2-(piperidinosulfonyl)-heptanoic acid
2-aminocarbonyl-5-(4-chlorophenyl)-pent-4-enoic acid
2-aminocarbonyl-7-(4-chlorophenyl)-2-methylheptanoic acid
2-aminocarbonyl-7-phenylheptanoic acid
2-aminocarbonyl-7-(4-methoxyphenyl)-heptanoic acid
2-aminocarbonyl-7-(4-methylphenyl)-heptanoic acid
2-aminocarbonyl-7-(3-trifluoromethylphenyl)-heptanoic acid
7-(4-chlorophenyl)-2-(phenylcarbonyl)-heptanoic acid
7-(4-chlorophenyl)-2-(dimethylaminocarbonyl)-heptanoic acid
7-(4-chlorophenyl)-2-(diethylaminocarbonyl)-heptanoic acid
7(4-chlorophenyl)-2-(phenylaminocarbonyl)-heptanoic acid
2-(benzylaminocarbonyl)-7-(4-chlorophenyl)-heptanoic acid
7-(4-chlorophenyl)-2-(morpholinocarbonyl)-heptanoic acid
7-(4-chlorophenyl)-2-(4-phenylpiperazinocarbonyl)-heptanoic acid
2-(4-benzylpiperazinocarbonyl)-7-(4-chlorophenyl)-heptanoic acid
5-(4-chlorophenyl-2-cyanopent-4-enoic acid
7-(4-chlorophenyl)-2-cyano-2-methylheptanoic acid
2-cyano-7-pentylheptanoic acid
2-cyano-7-(4-methoxyphenyl)-heptanoic acid
2-cyano-7-(4-methylphenyl)-heptanoic acid
2-cyano-7-(3-trifluoromethylphenyl)-heptanoic acid
7-(4-chlorophenyl)-2-(piperidinocarbonyl)-heptanoic acid
8-phenyl-2-(phenylsulfonyl)octanoic acid
8-(4-methoxyphenyl)-2-[(4-methylphenyl)sulfonyl]octanoic acid
2-[(4-methylphenyl)sulfonyl]-9-phenylnonanoic acid
10-phenyl-2-(phenylsulfonyl)decanoic acid 2-[(4-methylphenyl)sulfonyl]-12-phenyldodecanoic acid
6-(2-methoxyphenyl)-2-[(4-methylphenyl)sulfonyl]hexanoic acid
8-(2-methoxyphenyl)-2-[(4-methylphenyl)sulfonyl]octanoic acid
10-(2-methoxyphenyl)-2-[(4-methylphenyl)sulfonyl]decanoic acid
7-(2-methoxyphenyl)-2-(phenylsulfonyl)heptanoic acid
2-[(4-chlorophenyl)sulfonyl]-7-(2-methoxyphenyl)heptanoic acid
7-(2-methoxyphenyl)-2-[4-methoxyphenyl)sulfonyl]heptanoic acid
2-[(4-cyanophenyl)sulfonyl]-7-(2-methoxyphenyl)heptanoic acid
7-(5-chloro-2-methoxyphenyl)-2-(phenylsulfonyl)heptanoic acid
7-(5-chloro-2-methoxyphenyl)-2-[(4-methylphenyl)sulfonyl]heptanoic acid
7-(5-chloro-2-methoxyphenyl)-2-[(4-cyanophenyl)sulfonyl]heptanoic acid
7-(5-fluoro-2-methoxyphenyl)-2-[(4-methylphenyl)sulfonyl]heptanoic acid
7-(5-bromo-2-methoxyphenyl)-2-[(4-methylphenyl)sulfonyl]heptanoic acid
7-phenyl-2-(phenoxy)heptanoic acid
2-(4-methoxyphenoxy)-7-phenylheptanoic acid
2-(3-trifluoromethylphenoxy)-2-phenylheptanoic acid
2-(4-cyanophenoxy)-7-phenylheptanoic acid
2-(4-methylphenoxy)-8-phenyloctanoic acid
2-(4-methylphenoxy)-10-phenyloctanoic acid
10-(4-chlorophenyl)-2-(4-methylphenoxy)decanoic acid
7-(2-methoxyphenyl)-2-(4-methylphenoxy)heptanoic acid
8-(2-methoxyphenyl)2-(4-methylphenoxy)octanoic acid
7-(5-chloro-2-methoxyphenyl)-2-(4-methylphenoxy)heptanoic acid
7-phenyl-2-(phenylthio)heptanoic acid
2-[(4-chlorophenyl)thion]-7-phenylheptanoic acid
2-[(4-methoxyphenyl)thio]-7-phenylheptanoic acid
20-[(4-cyanophenyl)thio]-7-phenylheptanoic acid
2-[(4-methylphenyl)thio]-8-phenyloctanoic acid
2-[(4-methylphenyl)thio]-10-phenyldecanoic acid
8-(4-chlorophenyl)2-[(4-methylphenyl)thio]octanoic acid
10-(4-chlorophenyl)-2-[4-methylphenyl)thio]decanoic acid
7-(2-methoxyphenyl)-2-[(4-methylphenyl)thio]heptanoic acid
8-(2-methoxyphenyl)-2-[(4-methylphenyl)thio]octanoic acid
7-(5-chloro-2-methoxyphenyl)-2-[(4-methylphenyl)thio]heptanoic acid
5-phenyl-2-[(3-trifluoromethylphenyl)sulfonyl]pent-4-ynoic acid
2-[(4-methoxyl)sulfonyl]-5-phenyl-pent-4-ynoic acid
2-[(4-cyanophenyl)sulfonyl]-5-phenyl-pent-4-ynoic acid
2-[(4-methylphenyl)sulfonyl]-7-phenyl-hept-6-ynoic acid
5-(2-methoxyphenyl)-2-[(4-methylphenyl)sulfonyl]pent-4-ynoic acid
5-(5-chloro-2-methoxyphenyl)-2-[(4-methylphenyl)sulfonyl]-pent-4-ynoic acid
7-(4-chlorophenyl)-3.3-dimethyl-2-[(4-methylphenyl)sulfonyl]heptanoic acid
8-(4-chlorophenyl)-3.3-dimethyl-2-[(4-methylphenyl)sulfonyl]octanoic acid
10-(4-chlorophenyl)-3.3-dimethyl-2-[(4-methylphenyl)sulfonyl]decanoic acid
7-(4-chlorophenyl)-3.3-dimethyl-2-[4-methylphenyl)thio]heptanoic acid
8-(4-chlorophenyl)-3.3-dimethyl-2-[(4-methylphenyl)thio]octanoic acid
10-(4-chlorophenyl)-3.3-dimethyl-2-[(4-methylphenyl)thio]decanoic acid
7-(4-chlorophenyl)-3.3-dimethyl-2-(4-methylphenoxy)heptanoic acid
8-(4-chlorophenyl)-3.3-dimethyl-2-(4-methylphenoxy)octanoic acid
10-(4-chlorophenyl)-3.3-dimethyl-2-(4-methylphenoxy)decanoic acid
7-phenyl-2-[(2-phenylethyl)sulfonyl]heptanoic acid

We claim:

1. A carboxylic acid derivative of the formula:

$$R_1-A-\underset{\underset{X}{|}}{\overset{\overset{R^2}{|}}{C}}-COOH \quad (I)$$

wherein
$R_1$ is optionally substituted $C_6$–$C_{14}$-aryl or $C_6$–$C_{14}$-aryloxy wherein the substituents are hydroxy, halogen, $C_1$–$C_4$ alkyl, $C_1$–$C_4$ alkoxy, trifluoromethyl, cyano, nitro, amino or amino substituted once or twice by $C_1$–$C_4$ alkyl,
$R_2$ is hydrogen, or $R_1$-A-, A is a straight-chained or branched, saturated or unsaturated alkylene radical containing 3 to 8 carbon atoms, X is a radical of the formula —B—$R_3$ or —D—$NR_4R_5$, in which B is O, S, SO, $SO_2$, O(CO), $OSO_2$, or $NHSO_2$, D is $SO_2$ or CO,
$R_3$ is $C_1$–$C_8$ alkyl, trifluoromethyl, $C_5$–$C_7$ cycloalkyl, $C_6$–$C_{14}$ ara-$C_1$–$C_4$ alkyl, $C_6$–$C_{14}$ ara-$C_1$–$C_4$ alkenyl or $C_6$–$C_{14}$ aryl, the aryl moieties of which are optionally substituted with hydroxyl, halogen, $C_1$–$C_4$-alkyl, $C_1$–$C_4$-alkoxy, trifluoromethyl, cyano, nitro, amino or amino substituted once or twice by $C_1$–$C_4$ alkyl,
$R_4$ is hydrogen, $C_1$–$C_4$-alkyl or an optionally substituted $C_6$–$C_{14}$-aryl or $C_6$–$C_{14}$-ara-$C_1$–$C_3$-alkyl, the substituents being hydroxy, halogen, $C_1$–$C_4$ alkyl, $C_1$–$C_4$ alkoxy, trifluoromethyl, cyano, nitro, amino or amino substituted once or twice by $C_1$–$C_4$ alkyl,
$R_5$ is hydrogen or $C_1$–$C_4$-alkyl or a physiologically acceptable salt, ester, amide or nitrile thereof, with the proviso that:
when A is a —$CH_2$—$CH_2$—$CH_2$— or —CH=CH—$CH_2$— group or an aryl radical, $R_1$ cannot be an unsubstituted phenyl radical.

2. The carboxylic acid derivative of claim 1, wherein $R_1$ is a phenyl, naphthyl, phenyloxy or napthyloxy which are optionally substituted by hydroxyl, chloro, fluoro, $C_1$–$C_4$ alkyl, $C_1$–$C_4$ alkoxy, trifluoromethyl, cyano, nitro, amino, $C_1$–$C_4$ alkylamino or di-$C_1$–$C_4$-alkyl-amino, $R_2$ is hydrogen, or $R_1$-A- wherein A is a straight-chained, saturated or unsaturated alkylene radical containing 3 to 8 carbon atoms and X is carbonyl, $C_1$–$C_8$ alkoxy, $C_1$–$C_8$ alkyl-sulphenyl, $C_1$–$C_8$-alkyl-sulphinyl, $C_1$–$C_8$ alkylsulphonyl, trifluoromethylsulphonyl, phenoxy, phenylsulphenyl, phenylsulphinyl, phenylsulphonyl, naphthylsulphonyl, phenylethylenesulphonyl, phenylethenylsulphonyl, $C_1$–$C_8$-alkoxycarbonyloxy, $C_1$–$C_8$-alkylsulphonyloxy, $C_1$–$C_8$ alkyl-sulphonylamino, phenylcarbonyloxy, phenylsulphonyloxy, phenylsulphonylamino, aminosulphonyl, di-$C_1$-$C_8$-alkylaminosulphonyl, carbamoyl, di-$C_1$-$C_8$-alkylaminocarbonyl, phenylaminocarbonyl, benzylaminocarbonyl, the phenyl ring in all cases being optionally substituted by hydroxy, halogen, $C_1$-$C_4$-alkyl, $C_1$-$C_4$ alkoxy, trifluoromethyl, cyano, nitro, amino or amino substituted once or twice by $C_1$-$C_4$ alkyl or a physiologically acceptable salt, ester, amide or nitrile thereof.

3. The carboxylic acid derivative of claim 1 wherein $R_1$ is phenyl, 4-chlorophenyl, or 4-chlorophenoxy; A is an alkylene radical containing 3 to 8 carbon atoms or is —CH=CH—CH$_2$—, —CH$_2$—CH(CH$_3$)—CH$_2$—, —CH=C(CH$_3$)CH$_2$— or —C≡C—CH$_2$—, X is —OCH$_3$, —SCH$_3$, —SOCH$_3$, —SO$_2$CH$_3$, —SO$_2$CF$_3$, —O—phenyl, —S—phenyl, —SO—phenyl, —SO$_2$—phenyl, —SO$_2$—naphthyl, —SO$_2$CH$_2$—H$_2$—phenyl, —SO$_2$—CH=CH—phenyl, —OCOCH$_3$, —OSO$_2$CH$_3$, —NHSO$_2$CH$_3$, —OCO—phenyl, —OSO$_2$—phenyl, —NHSO$_2$—phenyl, —SO$_2$NH$_2$, —SO$_2$N(C$_2$H$_5$)$_2$, —CONH$_2$, —CON(CH$_3$)$_2$, —CO—N(C$_2$H$_5$)$_2$, —CO—NH—phenyl, or —CO—N—H—benzyl, whereby the phenyl ring is in all cases optionally substituted by hydroxyl, halogen, $C_1$-$C_4$ alkyl, $C_1$-$C_4$ alkoxy, trifluoromethyl, cyano, nitro, amino or amino substituted once or twice by $C_1$-$C_4$ alkyl, or a physiologically acceptable salt, ester, amide or nitrile thereof.

4. The carboxylic acid derivative of claim 1, wherein $R_1$ is a phenyl or phenyloxy which are optionally substituted by chloro, methyl, methoxy or trifluoromethyl.

5. The carboxylic acid derivative of claim 1, wherein A is a propylene, butylene or pentylene radical or is —CH=CH—CH$_2$—, —CH=C(CH$_3$)—CH$_2$— or —C≡C—CH$_2$.

6. The carboxylic acid derivative of claim 1, wherein $R_2$ is hydrogen or methyl.

7. The caboxylic acid derivative of claim 1, wherein B is SO$_2$, OSO$_2$, S or O and $R_3$ is phenyl optionally substituted with methyl, chloro, trifluoromethyl or methoxy.

8. The carboxylic acid derivative of claim 1 designated 5-(4-chlorophenyl)-2-(4-methylphenyl-sulphonyl)-pent-4-ynoic acid.

9. The carboxylic acid derivative of claim 1 designated methyl 7-(4-chlorophenyl)-2-(4-methylphenoxy)-heptanoate.

10. The carboxylic acid derivative of claim 1 designated 7-(4-chlorophenyl)-2-(4-methylphenoxy)-heptanoic acid.

11. The carboxylic acid derivative of claim 1 designated methyl 7-(4-chlorophenyl)-2-(4-methylphenylthio)-heptanoate.

12. The carboxylic acid derivative of claim 1 designated 7-(4-chlorophenyl)-2-(4-methylphenylthio)-heptanoic acid.

13. The carboxylic acid derivative of claim 1 designated ethyl 5-(4-chlorophenyl)-2-(4-methylphenylsulphonyl)-pent-4-ynoate.

14. A method of treating a diabetes, a prediabetes, an adipositas or an atherosclerosis ailment comprising administering to a patient suffering from said ailment an effective amount of the compound of the formula

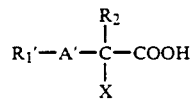

wherein
$R_1'$ is hydrogen or optionally substituted $C_6$-$C_{14}$-aryl or $C_6$-$C_{14}$-aryloxy wherein the substituents are hydroxy, halogen, $C_1$-$C_4$ alkyl, $C_1$-$C_4$ alkoxy, trifluoromethyl, cyano, nitro, amino or amino substituted once or twice by $C_1$-$C_4$ alkyl, $R_2'$ is hydrogen, $C_1$-$C_4$ alkyl or $R_1$—A';

A' is a straight-chained or branched, saturated or unsaturated alkylene radical containing 1 to 18 carbon atoms, X' is carbethoxy or a radical of the formula —B—$R_3$ or —D—NR$_4$R$_5$, in which B is O, S, SO, SO$_2$, O(CO), OSO$_2$, NHCO, NHSO$_2$ or CO and D is a valency bond, SO$_2$ or CO, $R_3$ is $C_1$-$C_8$ alkyl, trifluoromethyl, $C_5$-$C_7$ cycloalkyl, $C_6$-$C_{14}$-ara-$C_1$-$C_4$ alkyl, $C_6$-$C_{14}$ ara-$C_1$-$C_4$ alkenyl or $C_6$-$C_{14}$ aryl, the aryl moieties of which are optionally substituted with hydroxyl, halogen, $C_1$-$C_4$-alkyl, $C_1$-$C_4$-alkoxy, trifluoromethyl, cyano nitro, amino or amino substituted once or twice by $C_1$-$C_4$ alkyl, $R_4$ is hydrogen, $C_1$-$C_4$-alkyl or an optionally substituted $C_6$-$C_{14}$-aryl or $C_6$-$C_{14}$-ara-$C_1$-$C_3$-alkyl, the substituents being hydroxy, halogen, $C_1$-$C_4$ alkyl, $C_1$-$C_4$ alkoxy, trifluoromethyl, cyano nitro, amino or amino substituted once or twice by $C_1$-$C_4$ alkyl, $R_5$ is hydrogen or $C_1$-$C_4$-alkyl or a physiologically acceptable salt, ester, amide or nitrile thereof, in a pharmaceutically acceptable carrier to treat said ailment.

15. A method of treating a diabetes, a prediabetes, an adipositas or an aeherosclerosis ailment comprising administering to a patient suffering from said ailment, an effective amount of the compound of claim 1 to treat said ailment.

16. A method of treating a diabetes, a prediabetes, an adipositas or an atherosclerosis ailment comprising administering to a patient suffering from said ailment an effective amount of the carboxylic acid derivative designated 5-(4-chlorophenyl)-2-(4-methylphenylsulphonyl)-pent-4-ynoic acid; methyl 7-(4-chlorophenyl)-2-(4-methylphenoxy)-heptanoate; 7-(4-chlorophenyl)-2-(4-methylphenoxy)-heptanoic acid; methyl 7-(4-chlorophenyl)-2-(4-methylphenylthio)-heptanoate; 7-(4-chlorophenyl)-2-(4-methylphenylthio)-heptanoic acid; ethyl 5-(4-chlorophenyl)-2-(4-methylphenylsulphonyl)-pent-4-ynoate or ethyl 2-(4-methylphenylsulphonyl)-decanoate in a pharmaceutically acceptable carrier to treat said ailment.

17. A method of treating a diabetes, a prediabetes, an adipositas or an atherosclerosis ailment comprising administering to a patient suffering from said ailment an effective amount of the carboxylic acid derivative designated 5-(4-chlorophenyl)-2-(4-methylphenylsulphonyl)-pent-4-ynoic acid; methyl 7-(4-chlorophenyl)-2-(4-methylphenoxy)-heptanoate; 7-(4-chlorophenyl)-2-(4-methylphenoxy)-heptanoic acid; methyl 7-(4-chlorophenyl)-2(4-methylphenylthio)-heptanoate; 7-(4-chlorophenyl)-2-(4-methylphenylthio)-heptanoic acid or ethyl 5-(4-chlorophenyl)-2-(4-methylphenylsulphonyl)-pent-4-ynoate in pharmaceutically acceptable carrier to treat said ailment.

18. The method of claim 14 wherein 0.1 to 50 mg of salt compound is administered per kilogram of body weight.

19. A pharmaceutical composition for treating a diabetes, a prediabetes, an adipositas or an atherosclerosis ailment comprising an effective amount to treat said ailment of the carboxylic acid derivative of claim 14 in a pharmaceutically acceptable carrier.

20. A pharmaceutical composition for treating a diabetes, a prediabetes, an adipositas or an atherosclerosis ailment comprising an effective amount to treat said ailment of the carboxylic acid derivative of claim 1 in a pharmaceutically acceptable carrier.

21. A pharmaceutical composition for treating a diabetes, a prediabetes, an adipositas or an atherosclerosis ailment comprising an effective amount to treat said ailment of the carboxylic acid derivative of claim 1 designated 5-(4-chlorophenyl)-2-(4-methylphenyl-sulphonyl)-pent-4-ynoic acid; methyl 7-(4-chlorophenyl)-2-(4-methylphenoxy)-heptanoate; 7-(4-chlorophenyl)-2-(4-methylphenoxy)-heptanoic acid; methyl 7-(4-chlorophenyl)-2-(4-methylphenylthio)-heptanoate; 7-(4-chlorophenyl)-2-(4-methylphenylthio)-heptanoic acid or ethyl 5-(4-chlorophenyl)-2-(4-methylphenyl-sulphonyl)-pent-4-ynoate in a pharmaceutically acceptable carrier.

22. A pharmaceutical composition for treating a diabetes, a prediabetes, an adipositas or an atherosclerosis ailment comprising an effective amount to treat said ailment of the carboxylic acid derivative of claim 14 designated 5-(4-chlorophenyl)-2-(4-methylphenylsulphonyl)-pent-4-ynoic acid; methyl 7-(4-chlorophenyl)-2-(4-methylphenoxy)-heptanoate; 7-(4-chlorophenyl)-2-(4-methylphenoxy)-heptanoic acid; methyl 7-(4-chlorophenyl)-2-(4-methylphenylthio)-heptanoate; 7-(4-chlorophenyl)-2-(4-methylphenylthio)-heptanoic acid; ethyl 5-(4-chlorophenyl)-2-(4-methylphenylsulphonyl)-pent-4-ynoate or ethyl 2-(4-methylphenylsulphonyl)-decanoate in a pharmaceutically acceptable carrier.

* * * * *